US010449075B2

(12) United States Patent
Yu

(10) Patent No.: US 10,449,075 B2
(45) Date of Patent: Oct. 22, 2019

(54) BILIARY DIVERSION CATHETER

(71) Applicant: Steven Sounyoung Yu, Fairfax, VA (US)

(72) Inventor: Steven Sounyoung Yu, Fairfax, VA (US)

(*) Notice: Subject to any disclaimer, the term of this patent is extended or adjusted under 35 U.S.C. 154(b) by 216 days.

(21) Appl. No.: 15/381,027

(22) Filed: Dec. 15, 2016

(65) Prior Publication Data
US 2017/0165458 A1 Jun. 15, 2017

Related U.S. Application Data

(60) Provisional application No. 62/267,756, filed on Dec. 15, 2015.

(51) Int. Cl.
A61F 5/00 (2006.01)
A61M 27/00 (2006.01)
(Continued)

(52) U.S. Cl.
CPC ........ A61F 5/0013 (2013.01); A61B 17/1114 (2013.01); A61M 27/002 (2013.01);
(Continued)

(58) Field of Classification Search
CPC ................. A61B 17/11; A61F 5/0013; A61M 2025/0286; A61M 2025/0293;
(Continued)

(56) References Cited

U.S. PATENT DOCUMENTS 4,654,032 A * 3/1987 Morales-George ... A61M 25/02
604/174
6,267,988 B1 7/2001 Meyer
(Continued)

FOREIGN PATENT DOCUMENTS

WO WO 2012/007042 1/2012
WO WO 2012/007043 1/2012
(Continued)

OTHER PUBLICATIONS

Charles Flynn et al, "Bile diversion to the distal small intestine has comparable metabolic benefits to bariatric surgery" Nat. Commun. 2015, 6:7715.
(Continued)

Primary Examiner — Kai H Weng

(57) ABSTRACT

Biliary diversion catheters for diverting bile fluid from a part of the patient's biliary tree to the patient's distal small intestine. The catheter comprises a system of interconnected or interconnectable tubes: a biliary tube segment, an intestinal (e.g. ileal or jejunal) tube segment, and a flush tube segment. The biliary diversion catheter is designed such that bile fluid flows into the biliary tube segment and is shunted into the distal small intestine via the intestinal tube segment. The flush tube segment is used to infuse flush fluid into the catheter (e.g. to clear out any debris within the tube system of the catheter). The biliary tube segment and the intestinal tube segment may together form a drainage tube or an anastomotic component. The flush tube segment and the intestinal tube segment may together form a transabdominal tube.

20 Claims, 21 Drawing Sheets

(51) Int. Cl.
*A61B 17/11* (2006.01)
*A61M 39/22* (2006.01)
*A61M 25/02* (2006.01)

(52) U.S. Cl.
CPC ...... *A61B 2017/1139* (2013.01); *A61M 39/22* (2013.01); *A61M 2025/0286* (2013.01); *A61M 2025/0293* (2013.01); *A61M 2027/004* (2013.01); *A61M 2210/106* (2013.01); *A61M 2210/1075* (2013.01)

(58) Field of Classification Search
CPC ...... A61M 2027/004; A61M 2210/106; A61M 2210/1075; A61M 27/002; A61M 39/22
See application file for complete search history.

(56) References Cited

U.S. PATENT DOCUMENTS

| | | | |
|---|---|---|---|
| 7,452,363 | B2 | 11/2008 | Ortiz |
| 8,366,650 | B2 | 2/2013 | Young |
| 2005/0038415 | A1 | 2/2005 | Rohr et al. |
| 2005/0277900 | A1* | 12/2005 | Klein ................ A61F 5/003 604/318 |
| 2011/0100381 | A1 | 5/2011 | Elmer et al. |
| 2011/0106225 | A1 | 5/2011 | Elmer et al. |
| 2012/0172782 | A1 | 7/2012 | Thompson |
| 2013/0090590 | A1 | 4/2013 | Young et al. |
| 2014/0243665 | A1* | 8/2014 | Li ................ A61B 6/504 600/432 |

FOREIGN PATENT DOCUMENTS

| | | |
|---|---|---|
| WO | WO 2012/007044 | 1/2012 |
| WO | WO 2012/007045 | 1/2012 |
| WO | WO 2012/007047 | 1/2012 |
| WO | WO 2012/007052 | 1/2012 |
| WO | WO 2012/007053 | 1/2012 |
| WO | WO 2012/163415 | 12/2012 |
| WO | WO 2013/004262 | 1/2013 |
| WO | WO 2013/004263 | 1/2013 |
| WO | WO 2013/004264 | 1/2013 |

OTHER PUBLICATIONS

Rajendra Raghow, "Ménage-à-trois of bariatric surgery, bile acids and the gut microbiome" *World J Diabetes*. 2015, 6(3):367-370.
Sweeney et al, "Metabolic surgery: Action via hormonal milieu changes, changes in bile acids or gut microbiota? A summary of the literature" *Best Pract Res Clin Gastroenterol*. 2014, 28(4):727-740.
Pournaras et al, "The Role of Bile After Roux-en-Y Gastric Bypass in Promoting Weight Loss and Improving Glycaemic Control" *Endocrinology*. 2012, 153(8):3613-3619.

* cited by examiner

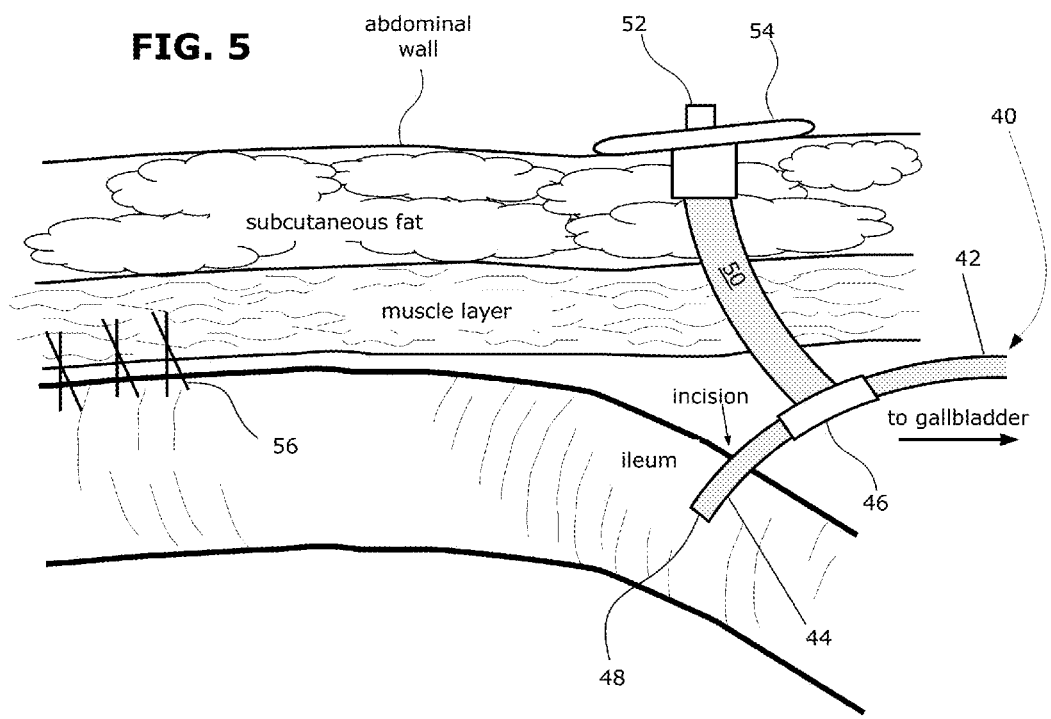
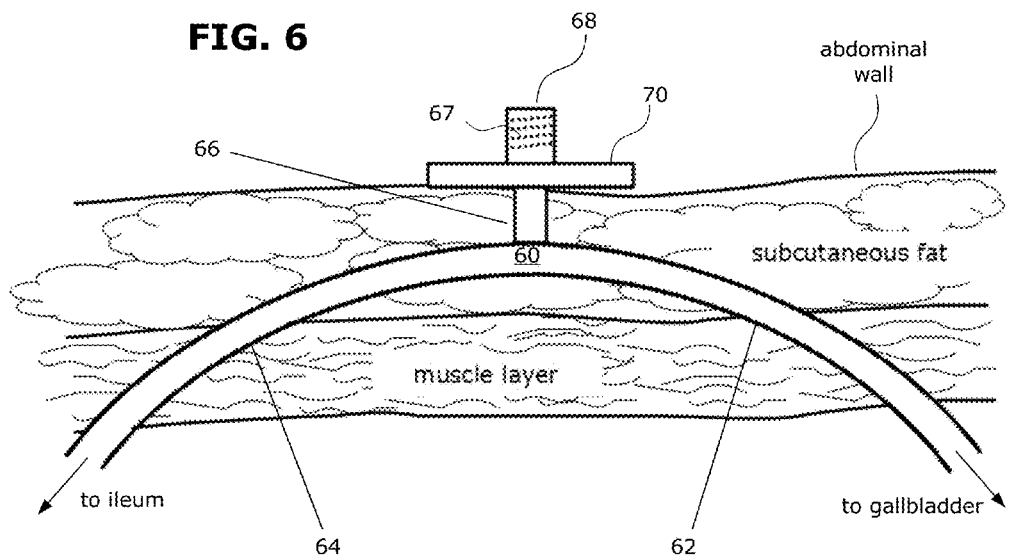

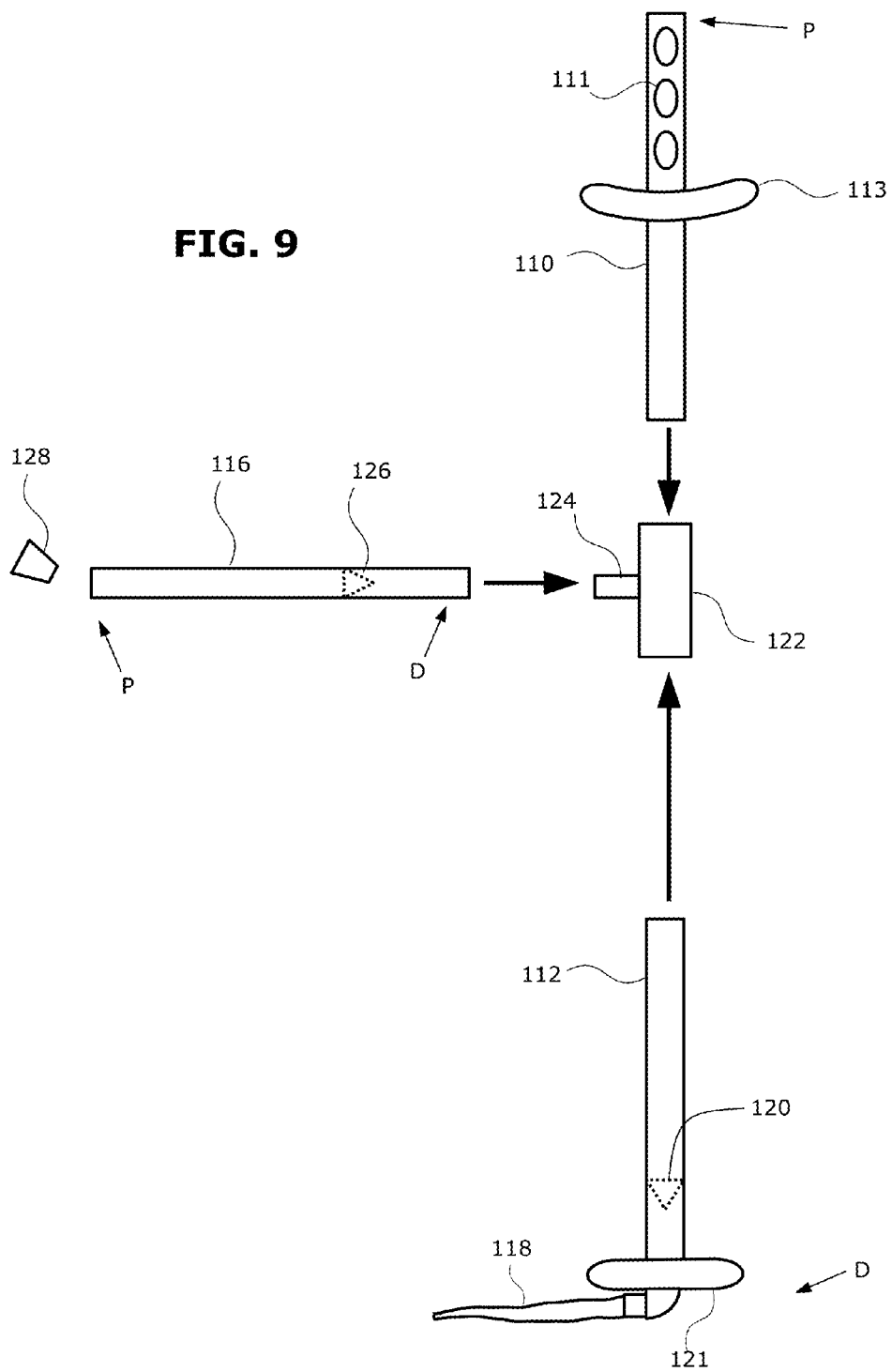

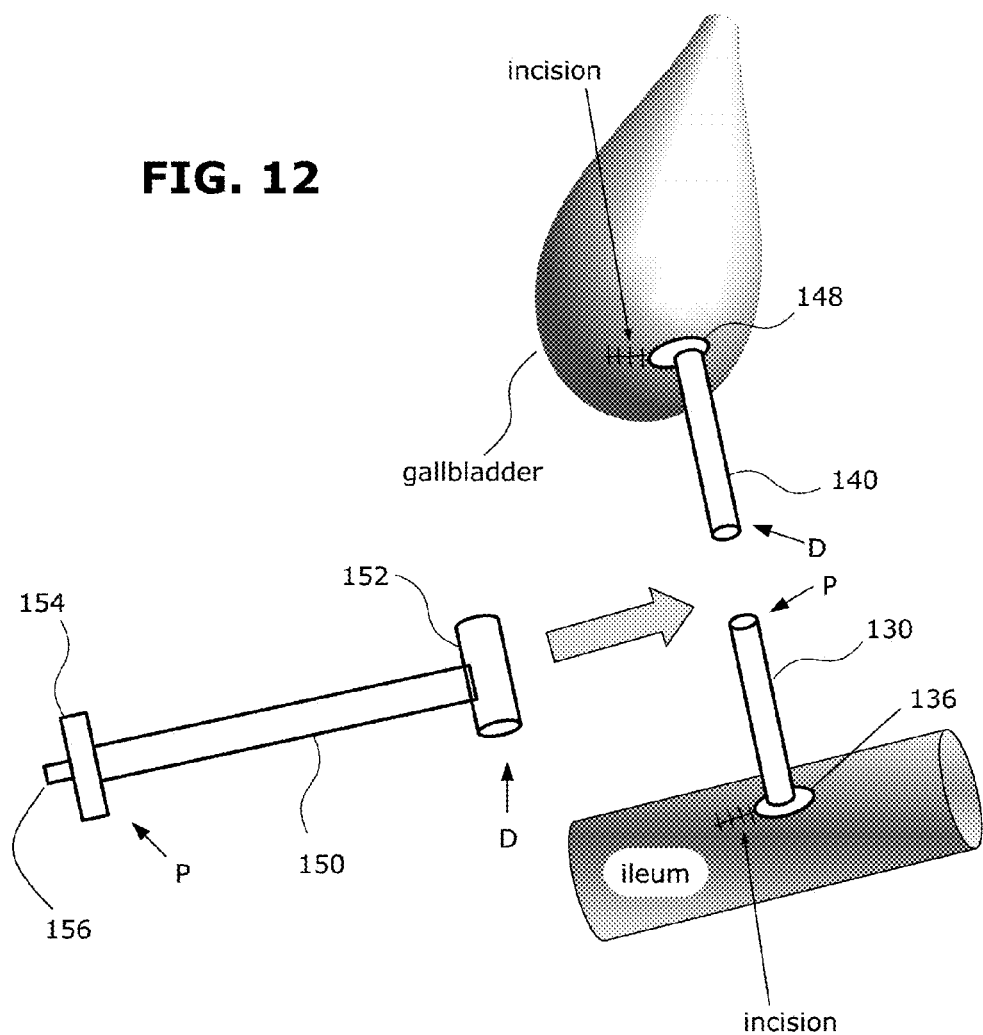

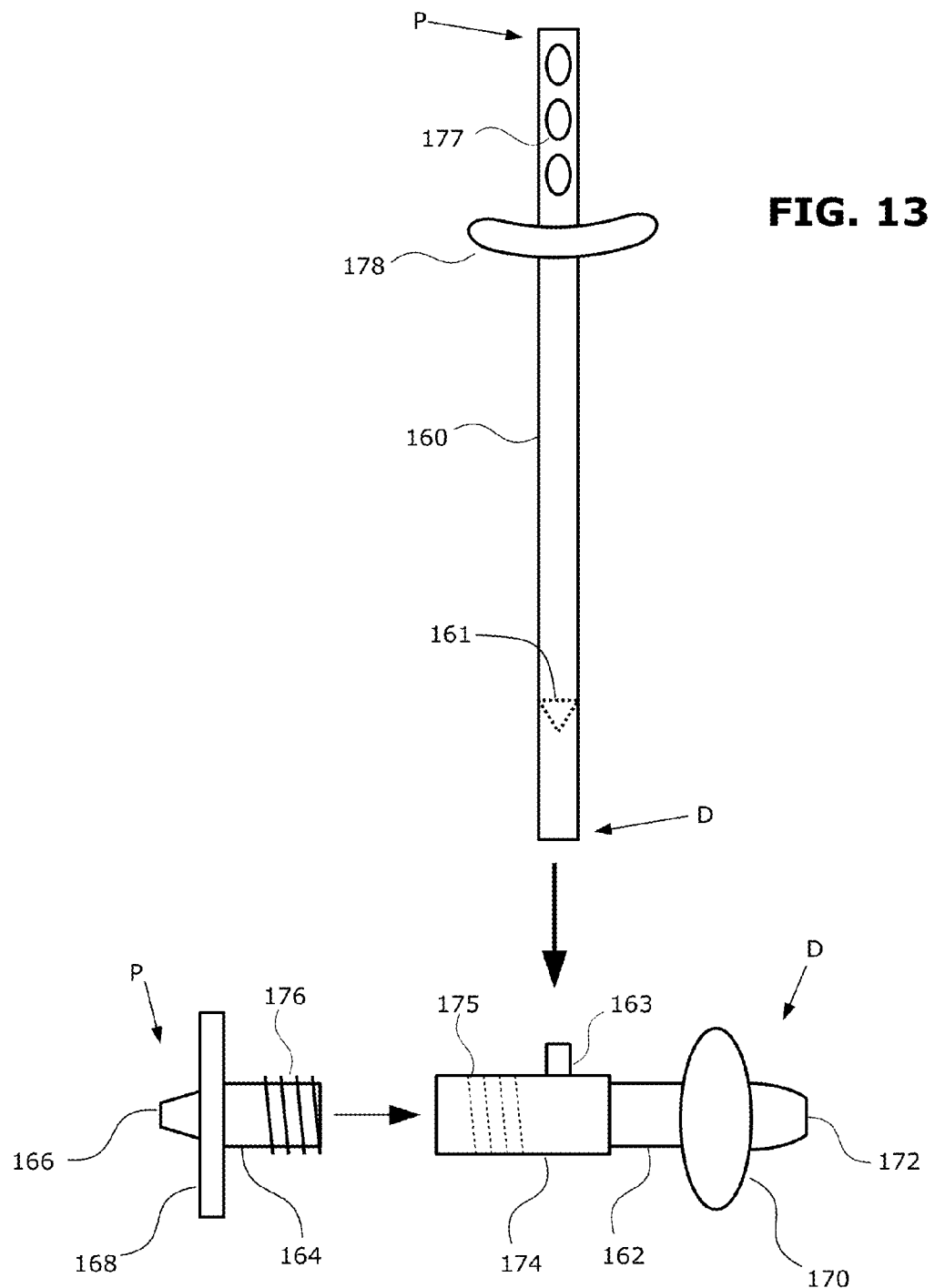

*drainage flow*

*reverse flow*

*forward flow*

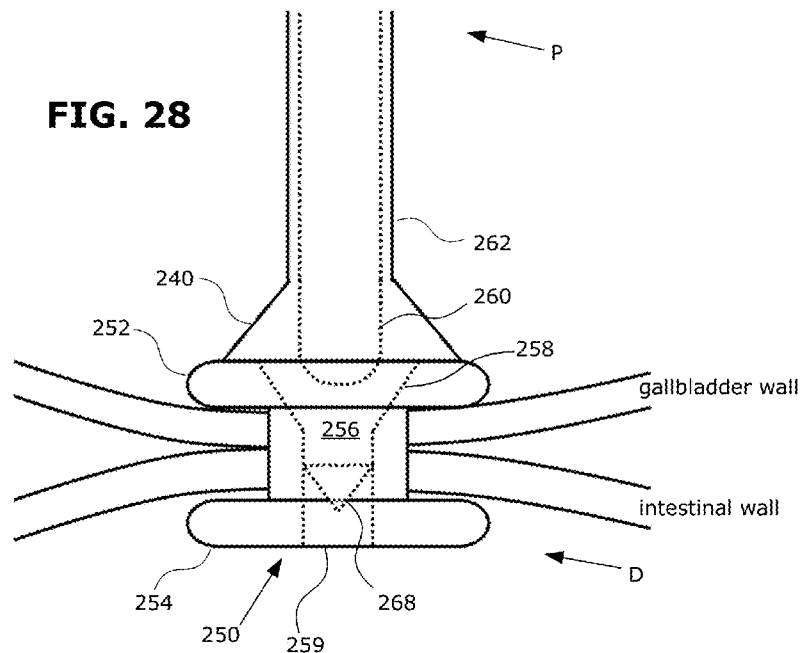
FIG. 28
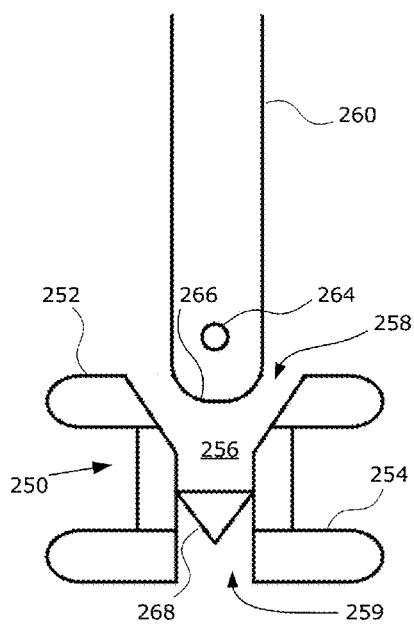
FIG. 29A
FIG. 29B

BILIARY DIVERSION CATHETER

TECHNICAL FIELD

This invention relates to catheters for bile fluid drainage.

BACKGROUND

With obesity approaching epidemic proportions, bariatric surgery has undergone steady growth worldwide. Diabetes is commonly associated with obesity. It is known that bariatric surgery can result in improvement in glycemic control and even remission of diabetes. However, the physiologic mechanism underlying this effect is unclear. Recently, it was found that bile diversion to the ileum results in physiologic changes similar to bariatric surgery, including sustained improvements in weight and glucose tolerance. See Charles Flynn et al, "Bile diversion to the distal small intestine has comparable metabolic benefits to bariatric surgery"//*Nature Communications* 6:7715 (July 2015). Thus, it is possible that bile diversion to the distal small intestine has metabolic benefits comparable to that of bariatric surgery

SUMMARY

Biliary Diversion Catheter.

In one embodiment, my invention can be described as a biliary diversion catheter that comprises a tube system. The tube system comprises a biliary tube segment, an intestinal (e.g. ileal or jejunal) tube segment, and a flush tube segment that are interconnected. The biliary tube segment has a proximal end, a distal end, and a proximal terminal portion encompassing its proximal end. The proximal terminal portion comprises an opening to allow inflow of bile fluid into the biliary tube segment.

The intestinal tube segment has a proximal end, a distal end, and a distal terminal portion that encompasses its distal end. The distal terminal portion comprises an opening to allow outflow of bile fluid. The intestinal tube segment is configured in the tube system such that it is in fluid communication with the biliary tube segment. The flush tube segment has a proximal end, a distal end, and a proximal terminal portion that encompasses its proximal end. The proximal terminal portion comprises an opening to receive flush fluid. The flush tube segment is configured in the tube system such that it is in fluid communication with at least the intestinal tube segment (and optionally, also the biliary tube segment).

In some embodiments, the proximal terminal portion of the biliary tube segment comprises a retention anchor. In some embodiments, the distal terminal portion of the intestinal tube segment comprises a retention anchor. In some embodiments, the proximal terminal portion of the flush tube segment comprises a retention anchor.

In some embodiments, the proximal terminal portion of the biliary tube segment comprises a retention means for retaining the terminal portion within the target site in the biliary tree. In some embodiments, the distal terminal portion of the intestinal tube segment comprises a retention means for retaining the terminal portion within the intestine. In some embodiments, the proximal terminal portion of the flush tube segment comprises a retention means to retain the terminal portion outside the abdominal cavity.

In some embodiments, the biliary tube segment comprises a one-way valve that facilitates the forward flow of fluid distally or resists the backflow of fluid proximally. In some embodiments, the intestinal tube segment comprises a one-way valve that facilitates the forward flow of fluid distally or resists the backflow of fluid proximally. In some embodiments, the flush tube segment comprises a one-way valve that facilitates the forward flow of fluid distally or resists the backflow of fluid proximally.

In some embodiments, the biliary tube segment and the intestinal tube segment together form a drainage tube, and the flush tube segment is connected with the drainage tube (e.g. as a branch off the drainage tube). In some embodiments, the flush tube segment and the intestinal tube segment together form a transabdominal tube. The biliary tube segment is connected with the transabdominal tube (e.g. as a branch off the transabdominal tube). In some embodiments, the length of the transabdominal tube is shorter than 10 cm; in some cases, its length is 1-7 cm.

In some embodiments, the biliary tube segment and the intestinal tube segment together form an anastomotic component, i.e. the anastomotic component comprises a biliary tube segment and an intestinal tube segment. The flush tube segment connects to the anastomotic component in a manner that allows flushing of at least the intestinal tube segment of the anastomotic component. In some cases, the biliary tube segment and the intestinal tube segment are provided separately. In such cases, the anastomotic component is assembled by connecting the biliary tube segment to the intestinal tube segment (e.g. by snapping them together).

Biliary Diversion Catheter.

In another embodiment, my invention can be described as a biliary diversion catheter that comprises a tube system. The tube system comprises a bile diversion means and a flushing means that are interconnected such that the flushing means is in fluid communication with at least a portion of the bile diversion means. A proximal terminal portion of the bile diversion means is inserted into a part of the biliary tree. A distal terminal portion of the bile diversion means is inserted into the distal small intestine. A proximal terminal portion of the flushing means is positioned outside the abdominal cavity. In operation, bile fluid is received into the bile diversion means and drained into the intestine. During flushing of the catheter, flush fluid that is infused into the flushing means from outside the abdominal cavity flows into the bile diversion means and out into the intestine (and optionally, also out into a part of the biliary tree).

In another embodiment, my invention can be described as a catheter kit comprising a bile diversion means and a flushing means. In another embodiment, my invention can be described as a method of assembling a catheter kit that comprises a bile diversion means and a flushing means. The method comprises connecting the bile diversion means with the flushing means. In some embodiments, this step of connecting is performed within the patient's abdominal cavity or abdominal wall. In some embodiments, this step of connecting is performed laparoscopically.

Catheter Kit.

In another embodiment, my invention can be described as a catheter kit comprising a drainage tube and a flush tube segment. The drainage tube has a proximal end and a distal end. There is a proximal terminal portion (at the biliary tube segment) that encompasses its proximal end and that comprises an opening for allowing the inflow of bile fluid. The distal terminal portion (at the intestinal tube segment) encompasses its distal end and comprises an opening to allow the outflow of bile fluid.

The flush tube segment has a proximal end and a distal end. There is a proximal terminal portion that encompasses its proximal end and that comprises an opening to receive flush fluid. The distal end of the flush tube segment is connectable with the drainage tube such that it is in fluid communication with the drainage tube.

In some embodiments, the drainage tube comprises a stem for connecting with the flush tube segment; in some cases, the stem comprises a one-way valve that facilitates the forward flow of fluid distally or resists the backflow of fluid proximally. In some embodiments, the flush tube segment comprises a retention anchor; in some cases, the kit further comprises a deployment instrument that can be passed through the flush tube segment to deploy the retention anchor on the flush tube segment.

In another embodiment, my invention can be described as a method of assembling a catheter kit that comprises a drainage tube and a flush tube segment. The method comprises connecting the drainage tube with the flush tube segment. In some cases, the step of connecting is performed within the patient's abdominal cavity or abdominal wall. In some cases, the step of connecting is performed laparoscopically.

Catheter Kit.

In another embodiment, my invention can be described as a catheter kit comprising a transabdominal tube and a biliary tube segment. The transabdominal tube has a proximal end and a distal end. There is a proximal terminal portion (at the flush tube segment) that encompasses its proximal end and that comprises an opening for receiving flush fluid. The distal terminal portion (at the intestinal tube segment) encompasses its distal end and comprises an opening to allow the outflow of bile fluid into the intestine.

The biliary tube segment has a proximal end and a distal end. There is a proximal terminal portion that encompasses its proximal end and that comprises an opening for allowing the inflow of bile fluid. The distal end of the biliary tube segment is connectable with the transabdominal tube such that the biliary tube segment is in fluid communication with the transabdominal tube.

In some embodiments, the transabdominal tube comprises a stem for connecting with the biliary tube segment; in some cases, the stem comprises a one-way valve that facilitates the forward flow of fluid distally or resists the backflow of fluid proximally. In some embodiments, the distal terminal portion of the transabdominal tube comprises a retention anchor; in some cases, the kit further comprises a deployment instrument that can be passed through the transabdominal tube to deploy the retention anchor.

In another embodiment, my invention can be described as a method of assembling a catheter kit that comprises a transabdominal tube and a biliary tube segment. The method comprises connecting the transabdominal tube with the biliary tube segment. In some cases, the step of connecting is performed within the patient's abdominal cavity or abdominal wall. In some cases, the step of connecting is performed laparoscopically.

Catheter Kit.

In another embodiment, my invention can be described as a catheter kit comprising a biliary tube segment, an intestinal (e.g. ileal or jejunal) tube segment, and a flush tube segment. The biliary tube segment has a proximal end and a distal end. There is a proximal terminal portion that encompasses its proximal end and that comprises an opening to allow inflow of bile fluid.

The intestinal tube segment has a proximal end and a distal end. There is a distal terminal portion that encompasses its distal end and comprises an opening to allow the outflow of bile fluid. In some embodiments, the proximal end of the intestinal tube segment is connectable with the distal end of the biliary tube segment such that it is in fluid communication with the biliary tube segment.

The flush tube segment has a proximal end and a distal end. There is a proximal terminal portion that encompasses its proximal end and that comprises an opening for receiving flushing fluid. The distal end of the flush tube segment is connectable with the biliary tube segment, the intestinal tube segment, or a joining segment between the intestinal tube segment and the biliary tube segment such that the flush tube segment is in fluid communication with at least the intestinal tube segment.

In some embodiments, the proximal end of the intestinal tube segment is connectable with the distal end of the flush tube segment. The distal end of the biliary tube segment is connectable with the flush tube segment, the intestinal tube segment, or a joining segment between the flush tube segment and the intestinal tube segment such that the biliary tube segment is in fluid communication with at least the intestinal tube segment.

In some embodiments, the flush tube segment comprises a retention anchor. In some embodiments, the intestinal tube segment comprises a retention anchor. In some cases, the kit further comprises a deployment instrument that can be passed through the flush tube segment to deploy the retention anchor on the flush tube segment or the intestinal tube segment.

In another embodiment, my invention can be described as a method of assembling a catheter kit that comprises a biliary tube segment, an intestinal tube segment, and a flush tube segment. These are assembled together to form a tube system. In some embodiments, the method comprises connecting the biliary tube segment with the intestinal tube segment to form a portion of the tube system. The method further comprises connecting the flush tube segment with that portion of the tube system, i.e. with the intestinal tube segment, or the biliary drainage tube, or a joining segment between the intestinal tube segment and the biliary tube segment. In some embodiments, the method comprises connecting the flush tube segment with the intestinal tube segment to form a portion of the tube system. The method further comprises connecting the biliary tube segment to that portion of the tube system, i.e. with the intestinal tube segment, or the flush tube segment, or a joining segment between the intestinal tube segment and the flush tube segment.

In some embodiments, the aforementioned steps of connecting are performed within the patient's abdominal cavity or abdominal wall. In some embodiments, these steps of connecting are performed laparoscopically.

Catheter Maintenance.

In another embodiment, my invention can be described as a method of performing maintenance on a biliary diversion catheter. In some embodiments, the method comprises flushing the catheter by infusing a volume of liquid medium into the flush tube segment. In some cases, the volume of liquid medium is 10-50 mls for each flush. In some cases, the liquid medium contains an enzyme (e.g. protease, lipase, cellulase, pancreatic enzyme, etc.). In some cases, this flushing procedure is performed once every T days, wherein T has a value of 1-4; in some cases, the flushing procedure is performed once daily. In some cases, the method comprises selectively flushing either the biliary tube segment or the intestinal tube segment.

The catheter may have a directional control valve as described above. In some cases, the method comprises: selecting a first directional pose for the directional control valve; selectively flushing the intestinal tube segment (by infusing a liquid medium as described above); selecting a second directional pose for the directional control valve; selectively flushing the biliary tube segment (by infusing a liquid medium as described above). Flushing of the intestinal tube segment and the biliary tube segment can be performed in either order. In some cases, the method comprises changing the directional pose of the directional control valve. This allows flushing of the intestinal tube segment and then, after changing the directional pose, flushing of the biliary tube segment; or alternatively flushing of the biliary tube segment and then flushing of the intestinal tube segment.

In some embodiments, the method of catheter maintenance comprises inserting an endoluminal cleaning tool into the flush tube segment. In another embodiment, my invention can be described as a catheter kit comprising a biliary diversion catheter and an endoluminal cleaning tool for cleaning the catheter.

Treatment Method.

In another embodiment, my invention can be described as a method of treating one or more medical conditions in a patient. The medical condition being treated can be a metabolic disorder such as obesity, dyslipidemia (e.g. hyperlipidemia), or elevated blood sugar (e.g. because of diabetes, insulin resistance, pre-diabetes, impaired glucose tolerance, etc.). The surgical methods of my invention can be performed by one or more medical personnel, which includes surgeons, nurses, physician assistants, surgical technicians, operating room technicians, manufacturer representatives, and other medical specialty personnel who work in the surgical operating room. The surgical methods of my invention can incorporate known surgical techniques, such as elements of the Witzel or Stamm enterostomy technique. The post-implantation maintenance of the catheter (e.g. daily saline flushes) can be performed by the patient or any other person (e.g. personal caretaker).

The treatment method comprises implanting a biliary diversion catheter as described herein into a patient's abdomen. In some embodiments, the implanting is performed laparoscopically. The proximal terminal portion of the biliary tube segment is inserted into a part of the patient's biliary tree. The distal terminal portion of the intestinal tube segment is inserted into the patient's distal small intestine. The proximal terminal portion of the flush tube segment is positioned outside the patient's abdominal cavity. In some embodiments, the method comprises assembling a catheter kit as described herein during the implantation.

The preceding summary is provided to organize the description in a manner that facilitates better understanding of my invention. It is not intended to be a complete, exhaustive list of all the embodiments that are possible in my invention.

BRIEF DESCRIPTION OF THE DRAWINGS

FIG. 5 shows another example of a biliary diversion catheter as fully implanted in the patient's abdomen.

FIG. 6 shows another example of a biliary diversion catheter as fully implanted in the patient's abdomen.

FIG. 9 shows an example of a biliary diversion catheter in which its tube system is provided as three separate components.

FIGS. 10A-10D, 11A-11D, and 12 show another example of a biliary diversion catheter and how it could be implanted using a laparoscopic surgery procedure. FIGS. 10A-10D show the ileal tube segment being implanted in the patient's ileum.

FIGS. 11A-11D show the biliary tube segment being implanted in the patient's gallbladder.

FIG. 12 shows the flush tube segment being attached to the biliary tube segment and the ileal tube segment.

FIG. 13 shows an example of a biliary diversion catheter in which its tube system is provided as three separate components.

FIGS. 19A and 19B show views of the directional control valve. FIGS. 20A-20C show the directional control valve in operation.

FIGS. 21A and 21B show perspective views of the directional control valve. FIGS. 22A-22C show the directional control valve in operation.

FIG. 28 shows another example of a biliary diversion catheter. FIGS. 29A and 29B show cross-section side views of the flush tube segment and anastomotic component.

DETAILED DESCRIPTION

Figure 1A:
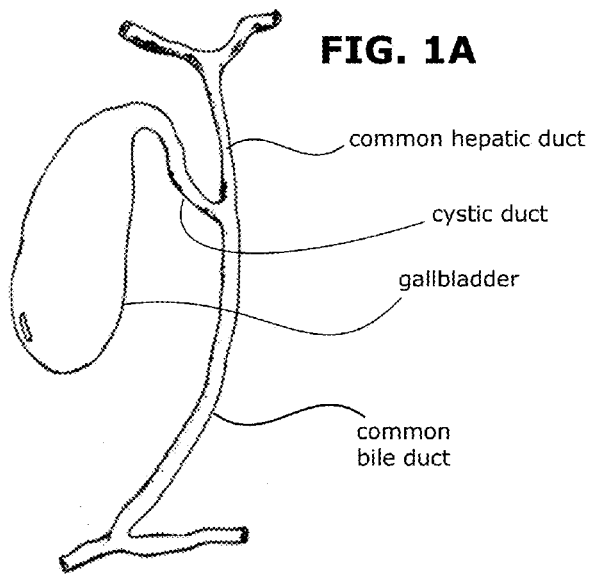
FIG. 1A shows the typical biliary tree anatomy.
Figure 1B:
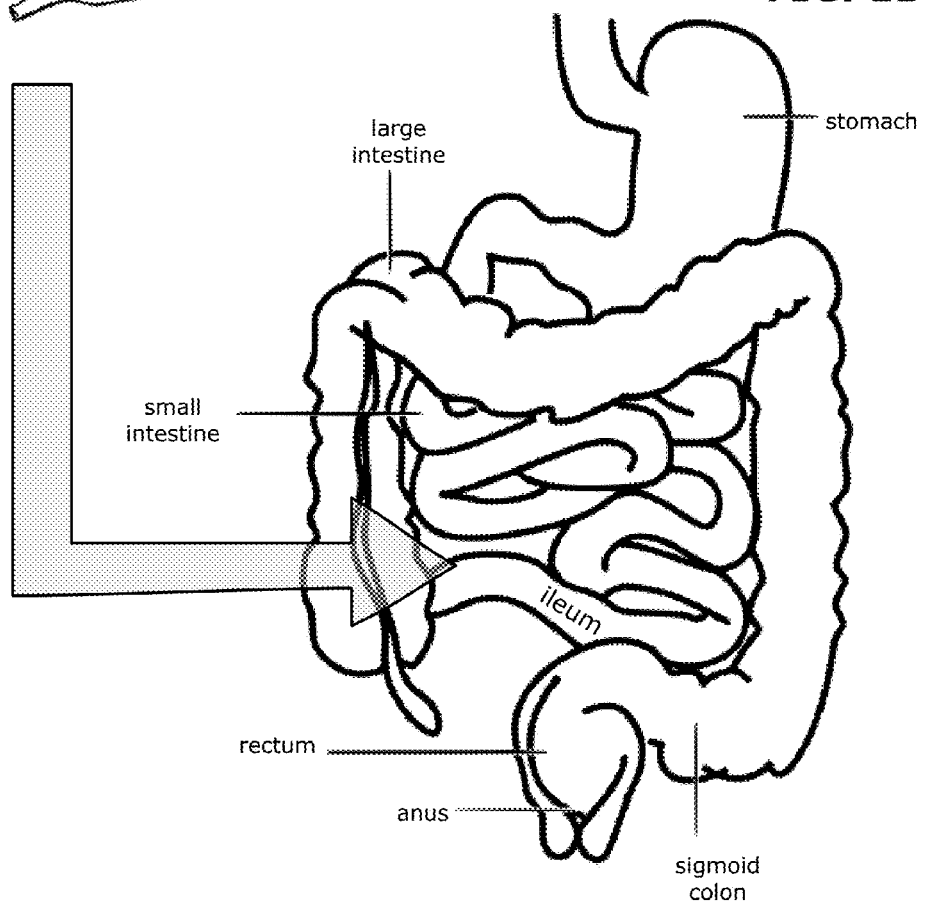
FIG. 1B shows the typical anatomy of the intestinal tract.

This invention relates to the diversion of bile fluid (all or a portion) from the patient's biliary system to the distal small intestine (e.g. ileum or jejunum). This bile fluid diversion is achieved using a bile diversion catheter, which extends from a part of the patient's biliary tree to the patient's distal small intestine (e.g. ileum or jejunum). As used herein, the term "biliary tree" includes the gallbladder and the bile ducts (cystic duct, left and right hepatic ducts, common hepatic duct, common bile duct, as well as other accessory or anatomically a typical bile ducts). To illustrate, FIG. 1A shows the typical biliary tree anatomy, including the gallbladder, cystic duct, left and right hepatic ducts, common hepatic duct, and common bile duct. FIG. 1B shows the typical anatomy of the intestinal tract, including the small intestine (with the ileum at its distal end) and large intestine.

The biliary diversion catheter comprises a system of interconnected or interconnectable tubes: a biliary tube segment, an intestinal (e.g. ileal or jejunal) tube segment, and a flush tube segment. The biliary diversion catheter is designed such that bile fluid flows into the biliary tube segment and is shunted into the distal small intestine via the intestinal tube segment. The terms "proximal" and "distal" are designated with respect to the intended direction of the fluid flow. In the context of this invention, fluid (e.g. bile fluid or flush fluid) flows from a proximal point to a distal point.

Biliary Tube Segment.

Towards its proximal end, the biliary tube segment comprises a terminal portion that resides within a part of the patient's biliary tree. At the proximal terminal portion, there are one or more openings that allow the inflow of bile fluid into the biliary tube segment. The opening may be located at any suitable place on the proximal terminal portion, such as at the proximal terminal end of the tube or other location on the tube. In some embodiments, the opening is located at the proximal end or within 3 cm of the proximal end of the biliary tube segment.

Intestinal Tube Segment.

Towards its distal end, the intestinal tube segment comprises a terminal portion that resides within the patient's distal small intestine (e.g. ileum or jejunum). At the distal terminal portion, there are one or more openings that allow the outflow of bile fluid into the distal small intestine. The opening may be located at any suitable place on the distal terminal portion, such as at the distal terminal end of the tube or other location on the tube. In some embodiments, the opening is located at the distal end or within 3 cm of the distal end of the intestinal tube segment. At its proximal end, the intestinal tube segment is interconnected or interconnectable with the tube system such that it is in fluid communication with the biliary tube segment.

Flush Tube Segment.

One of the problems that can arise is clogging of the catheter. This can result from the accumulation of debris, intestinal chyme, bile secretions, proteins, lipids, salts, bacteria, biofilm, or other causes. This clogging can obstruct the flow of bile fluid through the catheter. This obstruction can occur at any of various sites in the catheter, such as the biliary tube segment or the intestinal tube segment. Also, the presence of any valves in the catheter could increase the risk of clogging.

To address this problem, the catheter comprises a flush tube segment. Towards its proximal end, the flush tube segment comprises a proximal terminal portion that resides outside the patient's abdominal cavity, such as within the abdominal wall or at the skin surface. At the proximal terminal portion, there are one or more openings for receiving flush fluid into the flush tube segment. The opening may be located at any suitable place on the proximal terminal portion, such as at the proximal terminal end of the tube or other location on the tube. In some embodiments, the opening is located at the proximal end or within 3 cm of the proximal end of the flush tube segment.

At its distal end, the flush tube segment is interconnected or interconnectable with the tube system such that it is in fluid communication with at least the intestinal tube segment (and optionally, also the biliary tube segment). When flush fluid is infused into the opening, the flush fluid flows through the flush tube segment, into the intestinal tube segment, and out into the intestine. This flushing can help maintain the patency of the catheter.

In some embodiments, the opening can be opened/closed by user control (e.g. with an on/off valve). In some embodiments, the opening is adapted to be coupled with a syringe. For example, the opening can have a Luer connection that mates with a Luer-tipped syringe. In another example, the opening can be a stretchable elastic mouth at the end of the tube that can receive a syringe tip.

Openings.

The openings on the catheter can be any of various types. The opening may be the open terminal end of a tube (e.g. the mouth of the tube). The opening may be apertures on the tube such as fenestrations, perforations, holes, slits, passageways, cut-outs, etc. The opening may be part of a more complex structure such as being on an adaptor for a syringe or conventional intravenous line, being on a port for receiving a needle, being on a valve, or being associated with other fluid control components.

Retention Anchor.

One or more of the terminal portions of the catheter's tube system may have a tube retention anchor. The retention anchor helps retain the terminal portion of the tube segment within the lumen of the relevant body organ, or in the case of a proximal terminal portion of a flush tube segment, outside the abdominal cavity. The anchor may be axially slidable on the tube to allow for position adjustment.

The retention anchor can be a single unitary structure or an assembly of multiple (two or more) components. Examples of anchoring structures include bolsters, cuffs, buttons, rings, bumpers, fingers, fins, annulus, collars, shoulders, ledges, baskets, or coils. The anchor can have any suitable shape, such as circular or polygonal. In some embodiments, the anchor is radially expandable (with respect to the tube as the axis). Examples of radially expandable anchors include inflatable balloons, expandable mesh baskets, expandable cages, flexing fingers, etc.

In some embodiments, the retention anchor comprises one or more suture holding features that allows a suture to be passed through or around the retention anchor. Examples of suture holding features include holes, apertures, eyelets, indentations, recesses, grooves, tags, tabs, collars, rings, wings, fingers, knobs, bumps, hooks, posts, ridges, ribs, threading, tines, barbs, pins, or other such structures that can hold a suture. Having the retention anchor configured in this way can be useful in a variety of different circumstances, such as helping to secure the terminal portion of the tube on the relevant body organ, helping to secure the position of the body organ at a particular place within the abdomen, or helping to seal any incisions through which the tube is inserted.

Valves.

The catheter's tube system may also comprise one or more valves. The valves can be associated with the tube system in any suitable way, such as being formed on, connectable to, incorporated in, or attached to the tube system. In some embodiments, the tube system comprises one or more one-way check valves that facilitate the forward flow of fluid distally or resist the backflow of fluid proximally. Any suitable type of one-way valve can be used, including those described in WO 2012/007047 (Ethicon Endo-Surgery; by Michael Stokes et al.). Examples of types of one-way valves that can be used include ball shutter valves, flapper valves, umbrella valves, rolled tube valves, duckbill valves, and flexible diaphragm valves.

In some embodiments, the tube system comprises one or more control valves that can be operated to control the flow of the fluid. The valves can be operated by the user (e.g. the medical practitioner, patient, patient caretaker, or other person) in any suitable manner, such as manual actuation (e.g. with a lever, knob, or wheel) or electromechanical actuation (e.g. by a solenoid or servomotor). The control valve may be an on/off valve that opens and stops the flow of fluid. In some embodiments, the opening on the flush tube segment is controlled by an on/off control valve. For example, the on/off valve may be a user-controlled two-way valve with one position opening the valve and the other position closing the valve.

The control valve may be a directional control valve that can be operated to control the flow of fluid towards one or more directions within the tube system. In some cases, the directional control valve selectively directs the flow of flush fluid infused through the flush tube segment towards the intestinal tube segment only, or the biliary tube segment only, or either the intestinal tube segment or the biliary tube segment. The directional control valve may be located at any suitable place in the tube system, such as at the intestinal tube segment, or the biliary tube segment, or at the intersection of the flush tube segment with the tube system (e.g. at the intersection of the three tube segments). In some cases, the directional control valve is a multi-way (two or more) valve.

Cleaning Tool.

In some embodiments, an endoluminal cleaning tool can be inserted into the catheter via the flush tube segment to remove any obstructions inside the catheter. The endoluminal cleaning tool could be inserted through the same opening for infusing the flush fluid or through a different access route into the flush tube segment. The endoluminal cleaning tool may be able to reach into the biliary tube segment, the intestinal tube segment, or both. The cleaning tool has an elongate shape such as a rigid obturator, flexible wire, steerable cable, etc. that is small enough to be inserted into the catheter through the flush tube segment. The cleaning tool can be manipulated or actuated in any suitable way for cleaning the catheter, such as poking, scrubbing, grasping, flushing out, scraping, vacuuming, brushing, etc. To facilitate cleaning, the cleaning tool could be equipped with a brush, grasper jaws, mesh basket, rake, sonication probe, etc. The cleaning tool could also use fluid forces, such as vacuum suction or fluid irrigation, to facilitate cleaning. For example, the cleaning tool could have a vacuum line or an irrigation channel.

Miscellaneous.

The catheter can be made of any suitable material or combination of materials suitable for implantation, including silicone, polyethylene, polypropylene, polyurethane, butylated rubber, latex rubber, PTFE (polytetrafluoroethylene), stainless steel, titanium, etc. Whereas a portion(s) of the tube system resides within the lumen of a body organ, other portion(s) may reside outside the lumen of the intestinal tract or the biliary tree (extraluminal), such as the peritoneal space of the abdominal cavity, within the abdominal wall, or at the skin surface. The catheter may have a radiopaque marker for x-ray visualization. The inside of the tube system can be coated with PTFE, a hydrophilic coating, or other coating to aid the flow of bile fluid or resist degradative effects of bile fluid, chyme, or digestive secretions.

The length of the catheter's tube segments can depend on various design considerations such as how the catheter's tube system is configured, where or how the catheter is implanted, or the patient's body size. The diameter of the catheter's tube segments can depend on various design considerations such as reducing the risk of obstructions, providing sufficient flexibility, etc. Examples of sizes that can be used are 4-20 French sizes.

The biliary tube segment, intestinal tube segment, and flush tube segment can be connected and arranged in the tube system in any suitable configuration such that bile fluid flows into the biliary tube segment and is shunted into the distal small intestine via the intestinal tube segment; and flush fluid infused through the flush tube segment flows through at least the intestinal tube segment (and optionally, also through the biliary tube segment). The term "connectable" or "connected" in the context of the tube segments encompasses a direct connection between the tube segments as well as a connection via one or more joining segments. The connection can be in any suitable geometry, such as a T-configuration, Y-configuration, bifurcation, forked configuration, etc.

The biliary diversion catheter can be provided as a single assembly or as two or more separate components that are assembled together during the implantation procedure. In some embodiments, implantation of the catheter can be facilitated by having the tube system provided as two or more separate components that are assembled together when the catheter is implanted.

Figure 2:
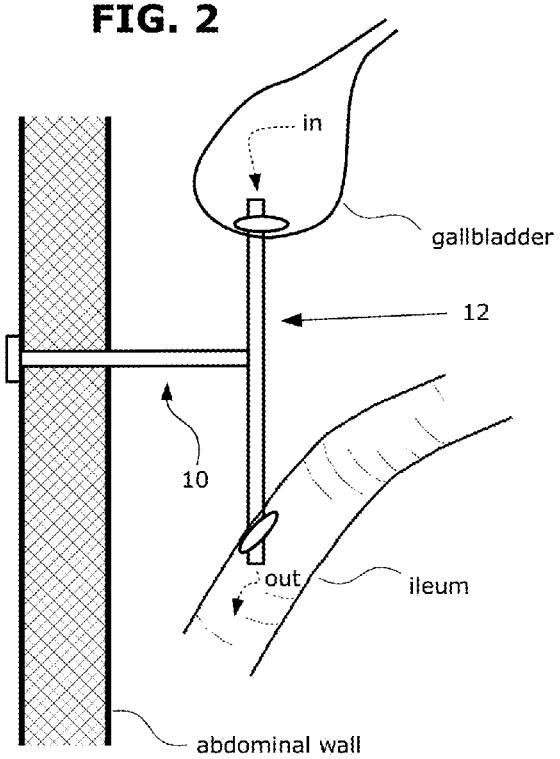
FIG. 2 shows a schematic diagram of an example biliary diversion catheter as arranged when implanted in the patient's abdomen.
Figure 3:
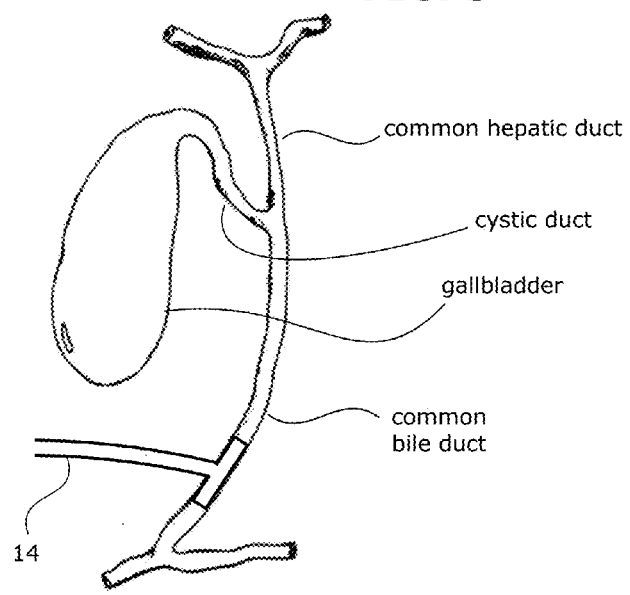
FIG. 3 shows an example in which the proximal terminal portion of a biliary tube segment has a T-tube configuration that is inserted into the common bile duct.

FIG. 2 shows a schematic diagram of an example catheter 10 of my invention as arranged when implanted in the patient's abdomen. One part of the catheter's tube system 12 extends from the gallbladder to the ileum of the small intestine. As indicated by the arrows, this part drains bile fluid from the gallbladder to the ileum. Another part of the catheter's tube system extends to the skin surface of the abdominal wall. This part provides external access for flushing of the catheter (e.g. with saline). FIG. 3 shows an example in which the proximal terminal portion of a biliary tube segment has a T-tube configuration 14 that is inserted into the common bile duct.

Drainage Tube Configuration.

In one embodiment of the catheter, the biliary tube segment and the intestinal tube segment together form a single tube structure (i.e. a drainage tube) that extends from its proximal end inside a part of the biliary tree to its distal end inside the distal small intestine. In this embodiment, the flush tube segment connects at an intermediate point on the drainage tube between the proximal and distal ends.

Figure 4A:
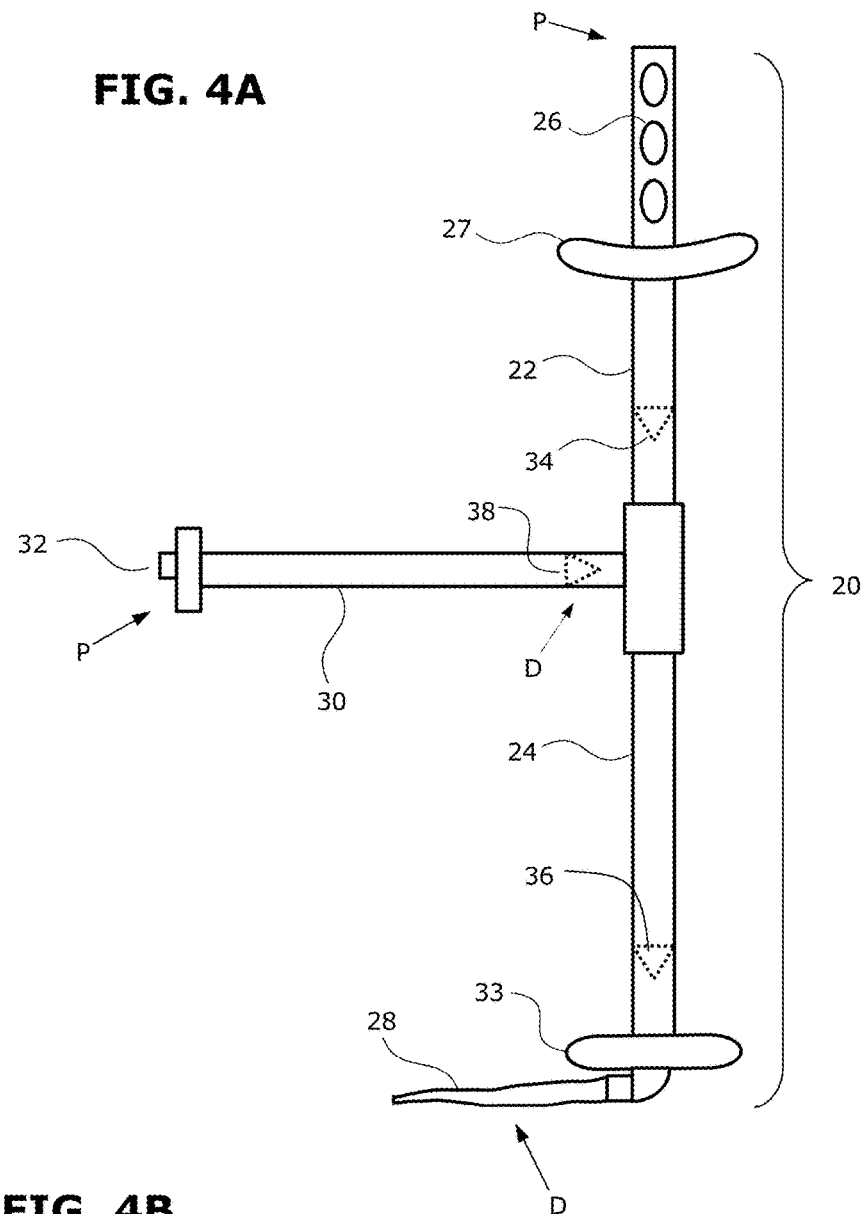
FIGS. 4A and 4B show another example of a biliary diversion catheter.
Figure 4B:
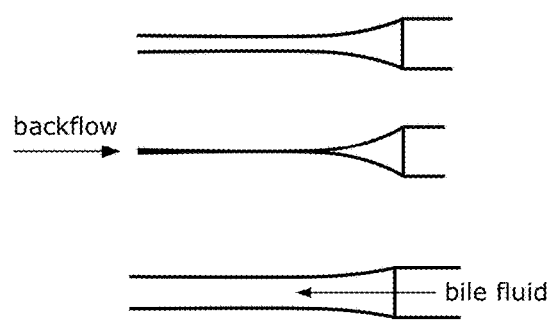

FIGS. 4A and 4B show another example of a catheter of my invention. In the drawing figures herein, "P" indicates the proximal end and "D" indicate the distal end. As shown in FIG. 4A, there is a drainage tube 20 which is comprised of a biliary tube segment 22 and an ileal tube segment 24. The proximal terminal portion of the drainage tube 20 (at its biliary tube segment 22) is for inserting into a patient's gallbladder. On this terminal portion are inlet perforations 26 for draining bile fluid. The biliary tube segment 22 has a circumferential cuff 27 that helps retain the terminal portion inside the gallbladder. The distal terminal portion of the drainage tube 20 (at its ileal tube segment 24) is for inserting into the patient's ileum. The ileal tube segment 24 has a circumferential cuff 33 that helps retain the distal terminal portion inside the ileum. At the distal end of the drainage tube 20, there is an outlet port provided on a collapsible duckbill valve 28 which allows outflow of bile fluid but prevents backflow of the small intestine contents. FIG. 4B shows how the duckbill valve 28 works. The duckbill valve 28 is a thin and flat-shaped rubber sleeve that collapses closed when there is no outflow of fluid. In the intestinal lumen, this prevents the backflow of intestinal contents through the valve. However, when bile fluid (or flush fluid) flows down through the ileal tube segment 24, the internal positive pressure causes the sleeve to open and allow the fluid to escape.

At its distal end, the flush tube segment 30 is connected as a branch off the drainage tube 20. The proximal terminal portion has a syringe fitting 32 for connecting with a syringe. A syringe filled with flush fluid (e.g. saline) is fitted to the syringe fitting 32 and the flush fluid is infused into the flush tube segment 30. The flush fluid then flows into the ileal tube segment 24 and out through the duckbill valve 28.

This catheter also includes several one-way check valves that help prevent backflow of intestinal contents. These one-way valves are represented as triangles in the drawing, with the point of the triangle indicating the direction in which fluid flow is facilitated (or against which backflow is resisted). There are two one-way check valves inside the drainage tube 20—one of the valves (34) is located proximally and the other (36) is located distally to the intersection with the flush tube segment 30. The one-way valves may be located at any suitable place within their respective tube segments. For example, one-way valve 36 may be located within 5 cm of the distal end of the drainage tube 20.

There is also a one-way valve 38 inside the flush tube segment 30. When saline or other flush fluid is injected into the flush tube segment 30 through the flush port, the saline flows down the flush tube segment 30 in the distal direction and enters the drainage tube 20. Within the drainage tube 20, the proximally-located one-way valve 34 blocks the flow of saline in the proximal direction of the drainage tube 20, forcing the saline to instead flow through the ileal tube segment 24 and out into the ileum.

FIG. 5 shows another example of a catheter as fully implanted in the patient's abdomen. This is a cross-section view of one particular section of the abdominal wall and the ileum showing the catheter implanted inside the abdomen. This section of the abdominal wall has a superficial layer of subcutaneous fat, and a deeper-lying muscle layer. There is a layer of fascia in between. During implantation, a portion of the ileum near to where the catheter is implanted is fixed to the abdominal wall via the anchoring stitches 56. Attaching the ileum to the abdominal wall in this manner helps to prevent torsion of the small intestine.

As seen here, the catheter comprises a drainage tube 40 (which comprises a biliary tube segment 42 and an ileal tube segment 44 connected across a joint 46). The distal end of the drainage tube 40 is inserted into the ileum through a small incision. The proximal end of the drainage tube 40 is inserted into the gallbladder (not shown). Bile fluid in the gallbladder flows into the biliary tube segment 42 and drains out the exit port 48 at the distal end of the drainage tube 40 at its ileal tube segment 44. A flush tube segment 50 branches off the drainage tube 40 from its intersection joint 46. The proximal end of the flush tube segment 50 is fitted with a syringe connector 52 for attaching a syringe filled with flush fluid. A wide-base external retainer 54 on the syringe connector 52 is stitched onto the skin to fix its position and help keep the syringe connector 52 at the skin surface (instead of being withdrawn into the abdominal wall). When flush fluid is infused into the flush tube segment 50, the flush fluid flows towards the ileal tube segment 44, or towards the biliary tube segment 42, or both depending on the directional configuration of any valves inside the tube system.

FIG. 6 shows another example of a catheter as fully implanted in the patient's abdomen. This is a cross-section view of the abdominal wall and the ileum showing the catheter implanted inside the abdomen. This catheter comprises a drainage tube 60 (which comprises a biliary tube segment 62 and an ileal tube segment 64). An intermediate portion of the drainage tube travels through a tunnel created within the abdominal wall. This helps secure the drainage tube 60 to restrict excessive movement inside the abdominal cavity.

On the left side of the drawing, the ileal tube segment 64 exits out of the tunnel into the peritoneum. The distal terminal portion of the ileal tube segment 64 (not shown) is inserted into the ileum. On the right side of the drawing, the biliary tube segment 62 exits out of the tunnel into the peritoneum. The proximal terminal portion of the biliary tube segment 62 (not shown) is inserted into the gallbladder (not shown). Bile fluid in the gallbladder flows into the biliary tube segment 62 and drains out into the ileum via the ileal tube segment 64.

The flush tube segment connects to the drainage tube 60 at the intermediate portion that travels through the tunnel within the abdominal wall. The proximal terminal portion of the flush tube segment 66 rests on the skin surface of the abdominal wall. On this proximal terminal portion, there is a Luer connector 68 with internal threads 67 to connect with a Luer adaptor on a syringe or conventional intravenous (IV) line for infusing flush fluid. A plastic disc 70 fitted around Luer connector 68 helps retain it at the skin surface (instead of being withdrawn into the abdominal wall). When flush fluid is infused into the flush tube segment 66, the flush fluid flows towards the ileal tube segment 64, or towards the biliary tube segment 62, or both depending on the directional configuration of any valves inside the tube system.

Transabdominal Tube Configuration.

In another embodiment of the catheter, the flush tube segment and the intestinal tube segment together form a single tube structure (i.e. a transabdominal tube) that extends from its proximal end outside the abdominal cavity to its distal end inside the distal small intestine. In this embodiment, the biliary tube segment connects at an intermediate point on the transabdominal tube between its proximal and distal ends.

Figure 7:
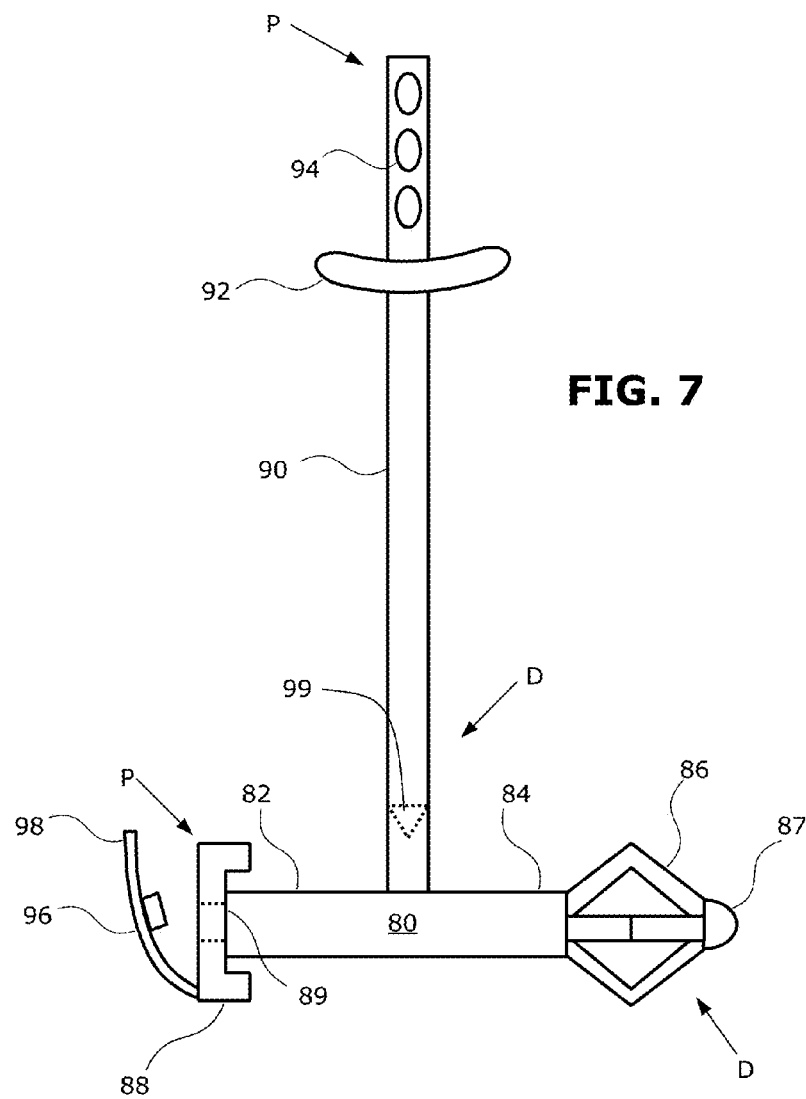
FIG. 7 shows another example of a biliary diversion catheter.

FIG. 7 shows another example of a catheter of my invention. There is a transabdominal tube 80 that is comprised of a flush tube segment 82 and an ileal tube segment 84. The transabdominal tube 80 traverses through the abdominal wall. The distal terminal portion of the transabdominal tube 80 (at its ileal tube segment 84) is for inserting into the patient's ileum. At its distal end, the transabdominal tube 80 has an outlet port (not shown) for outflow of bile fluid. Also, the distal end is fitted with an expandable cage 86 that helps to retain the distal terminal portion inside the intestine.

The proximal terminal portion of the transabdominal tube 80 (at its flush tube segment 82) is positioned at the skin surface outside the abdominal wall. The proximal terminal portion is fitted with a bolster 88 to help retain it at the skin surface. At the center of the bolster 88, there is a syringe port 89 for inserting the tip of a syringe that is filled with flush fluid. The biliary tube segment 90 is connected as a branch off the transabdominal tube 80. The proximal terminal portion of the biliary tube segment 90 is inserted into the gallbladder. At this terminal portion, there is a circumferential cuff 92 that helps retain the terminal portion inside the gallbladder and inlet perforations 94 for draining bile fluid.

When not in use, the syringe port 89 is plugged by a cap 96 held onto the bolster 88 by a flexible tether 98. To flush the catheter, the user uncaps the syringe port 89, fits the syringe tip into the syringe port 89, and infuses the flush fluid. There is a one-way valve 99 in the biliary tube segment 90 such that the infused flush fluid is directed towards the ileal tube segment 84 and out into the ileum. This one-way valve 99 also serves to reduce any backflow of intestinal contents into the biliary tube segment 90.

Figure 8:
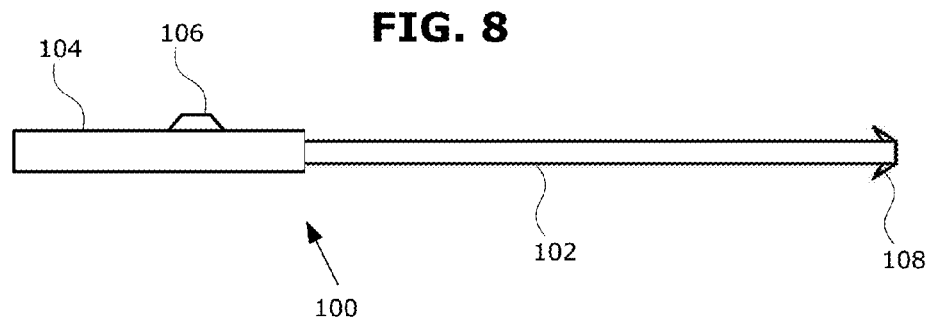
FIG. 8 shows an example of a deployment instrument.

In some embodiments, a deployment instrument can be inserted through the flush tube segment to deploy a retention anchor on the flush tube segment or the ileal tube segment. FIG. 8 shows an example of a deployment instrument 100 that could be used to deploy the expandable cage 86 on the catheter shown in FIG. 7. The deployment instrument 100 has an obturator rod 102 attached to a handle 104. The cap 96 on the transabdominal tube 80 is opened and the obturator rod 102 is inserted through the syringe port 89 into the transabdominal tube 80. The obturator rod 102 is advanced until the tip of the rod 102 engages with the locking hub 87 on the expandable cage 86. When the actuator button 106 on the handle 104 is pushed, this causes the fins 108 at the tip of the rod 102 to flare out and latch onto the locking hub 87. After latching onto the locking hub 87, the deployment instrument 100 is pulled backwards, which flexes the hinge arms outward and radially expands the expandable cage 86. With twisting of the obturator rod 102, the locking hub 87 locks the cage 86 in its expanded state.

Anastomotic Device Configuration.

In some embodiments, the biliary tube segment and the intestinal tube segment together form an anastomotic component. The anastomotic component has a channel that creates an anastomosis between the lumen of the biliary tree and the intestinal lumen. Examples of anastomotic components that could be used include those described in patent publications WO 2012/007044 (Alessandro Pastorelli et al.); WO 2012/007047 (Michael Stokes et al.); WO 2012/007045 (James Voegele et al.); WO 2012/007052 (Manoel Galvao et al.); WO 2012/007042 (Mark Steven Ortiz et al.); WO 2013/004263 (Alberto Arezzo et al.); WO 2013/004264 (Alessandro Pastorelli et al.); and U.S. Pat. No. 8,535,259 (Suzanne Thompson); all of which are incorporated by reference herein.

The biliary tube segment has a proximal end and a proximal terminal portion encompassing its proximal end. The proximal terminal portion of the biliary tube segment resides inside a part of the patient's biliary tree. The proximal terminal portion comprises an opening to allow inflow of bile fluid into the anastomotic component. The intestinal tube segment has a distal end and a distal terminal portion that encompasses its distal end. The distal terminal portion of the intestinal tube segment resides inside the distal small intestine. The distal terminal portion comprises an opening to allow outflow of bile fluid Bile fluid enters through the opening in the proximal terminal portion and drains out of the opening in the distal terminal portion and into the small intestine. In some embodiments, there is a one-way valve within the channel of the anastomotic component. The one-way valve directs the flow of fluid distally towards the opening at the distal terminal portion and resists the backflow of fluid proximally. In some embodiments, the one-way valve is located in the intestinal tube segment.

The flush tube segment connects to the anastomotic component to allow flushing of at least the intestinal tube segment of the anastomotic component (and optionally, also the biliary tube segment). In some cases, the tube system is configured such that the flush tube can also be used to flush the biliary tube segment of the anastomotic component. In some cases, the tube system is configured such that the flush tube can selectively flush either the biliary tube segment or the intestinal tube segment of the anastomotic component. The tube system can have any suitable design that allows the flush tube to selectively flush either the biliary tube segment or the intestinal tube segment of the anastomotic component, such as using a directional control valve within the tube system.

FIG. 28 shows another example of a biliary diversion catheter of my invention. The catheter comprises an anastomotic component 250 that is comprised of a biliary tube segment 252 and an intestinal tube segment 254. The anastomotic component 250 traverses and joins the gallbladder wall and intestinal wall. The channel 256 within the anastomotic component 250 creates an anastomosis between the gallbladder and intestine. Proximally on the biliary tube segment 252, the anastomotic component 250 has an opening 258 for receiving bile fluid from the gallbladder. Distally on the intestinal tube segment 254, the anastomotic component 250 has an opening 259 for draining the bile fluid into the distal small intestine. Within the channel 256 of the intestinal tube segment 254, there is a one-way valve 268 that directs the flow of bile fluid distally.

The catheter further comprises a flush tube segment 260 for flushing the anastomotic component 250. The flush tube segment 260 is contained within a sleeve 262 such that the flush tube 260 can be advanced or retracted relative to the anastomotic component 250. At its distal end, the sleeve 262 forms a canopy-like enclosure 240 having slits to allow inflow of bile fluid so that it can drain into opening 258. The flush tube segment 260 has a side opening 264 and a distal tip opening 266 (not shown in this view). Within flush tube segment 260, there is a fluid passageway for side opening 264 and a separate fluid passageway for distal tip opening 266. The fluid passageways are connected to external openings on the proximal terminal portion (not shown) of the flush tube segment 260. With the separate passageways, the user can selectively infuse flush fluid to spray out of side opening 264 or distal tip opening 266.

FIGS. 29A and 29B show cross-section side views of the flush tube segment 260 and anastomotic component 250 in isolation to demonstrate its manner of operation. In FIG. 29A, the flush tube segment 260 is in a retracted configuration, which allows bile fluid to flow into the anastomotic component 250 through its proximal opening 258. In FIG. 29B, the flush tube segment 260 is advanced to seal the channel 256. After sealing channel 256, the user can infuse flush fluid through the flush tube segment 260 to selectively spray flush fluid out of side opening 264 to flush the biliary tube segment 252 or out of distal tip opening 266 to flush the intestinal tube segment 254.

Separate Components.

In some embodiments, the tube system is provided as at least three separate tube components that are assembled together when the catheter is implanted. FIG. 9 shows an example of a catheter in which its tube system is provided as three separate components: a biliary tube segment 110, an ileal tube segment 112, and a flush tube segment 116 that are assembled together when the catheter is implanted. Regarding the biliary tube segment 110, the terminal portion towards the proximal end is for inserting into the patient's gallbladder. On this terminal portion are inlet perforations 111 for draining bile fluid and a circumferential cuff 113 that helps retain the terminal portion inside the gallbladder. Regarding the ileal tube segment 112, the terminal portion towards the distal end is for inserting into the patient's ileum. There is a cuff 121 that helps retain the terminal portion inside the ileum. At the distal end, there is an outlet port on a collapsible duckbill valve 118 which allows outflow of bile fluid but prevents backflow of intestinal contents. There is also a one-way valve 120 in the ileal tube segment 112 to further impede backflow of intestinal contents.

During implantation, the distal end of biliary tube segment 110 is connected to the proximal end of the ileal tube segment 112 via a coupling 122. The flush tube segment 116 is also connected to the coupling 122 fitting via the stem 124. Flush fluid can be infused through the open proximal end of the flush tube segment 116. There is a one-way valve 126 in the flush tube segment 116 to resist backflow of flush fluid. After the flushing procedure is completed, the opening is shut with a cork 128.

Figure 10A:
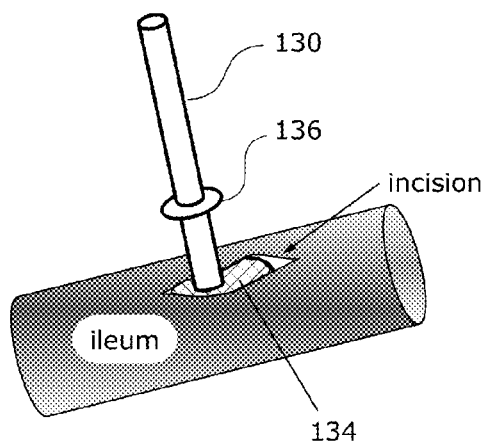
Figure 10B:
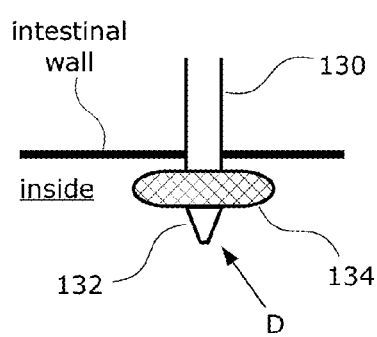
Figure 10C:
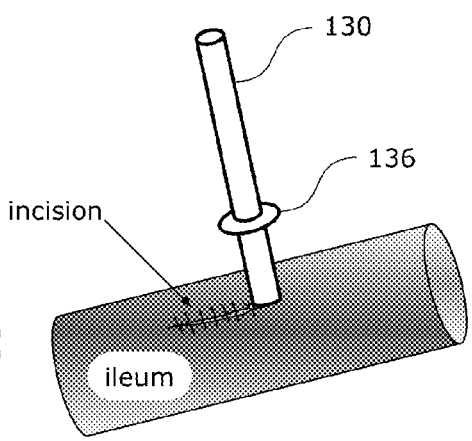
Figure 10D:
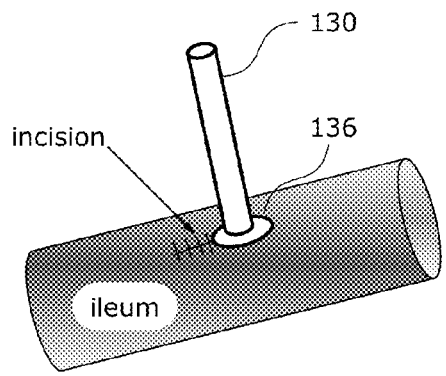

FIGS. 10A-10D, 11A-11D, and 12 show another example of a catheter and how it could be implanted using a laparoscopic surgery procedure. The catheter's tube system is provided as three separate components: a biliary tube segment 140, an ileal tube segment 130, and a flush tube segment 150 that are assembled together when the catheter is implanted. FIGS. 10A-10D show the ileal tube segment 130 being implanted in the patient's ileum. FIG. 10A shows a portion of the ileum into which the catheter is implanted. The surgeon makes a small incision into the ileum and inserts the distal terminal portion of the ileal tube segment 130 into the ileum through the incision. FIG. 10B shows a cross-section side view to illustrate how the terminal portion of the ileal tube segment 130 resides in the ileum (shown by the intestinal wall). The distal end of the ileal tube segment 130 has a duckbill valve 132 that drains bile fluid into the ileum. The internal bolster 134 on the ileal tube segment 130 anchors it inside the intestinal lumen. As shown in FIG. 10C, the incision is sutured closed to seal the terminal portion of the ileal tube segment 130 inside the ileum. As shown in FIG. 10D, a slidable washer 136 fitted around the tube segment is pushed down onto the incision and glued onto the suture site with an adhesive to further improve the seal.

Figure 11A:
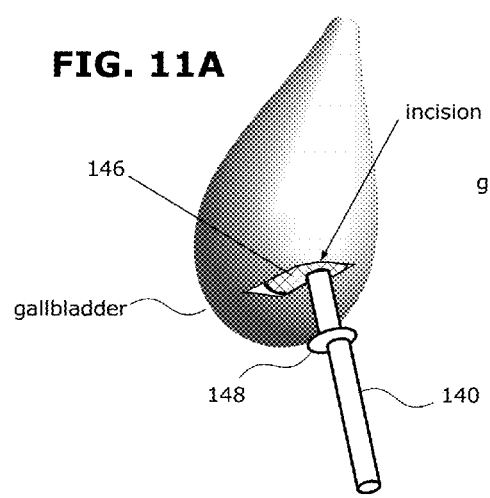
Figure 11B:
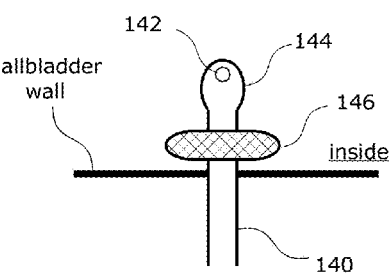
Figure 11C:
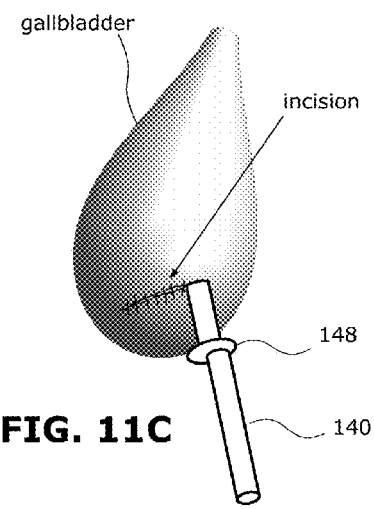
Figure 11D:
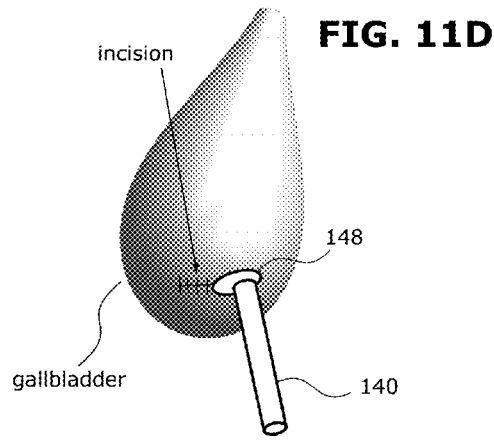

FIGS. 11A-11D show the biliary tube segment 140 being implanted in the patient's gallbladder. FIG. 11A shows the patient's gallbladder into which the catheter is implanted. The surgeon makes a small window incision into the fundus of the gallbladder and inserts the terminal portion of the biliary tube segment 140 into the gallbladder through the incision. FIG. 11B shows a cross-section side view to illustrate how the terminal portion of the biliary tube segment 140 resides in the gallbladder (shown by the gallbladder wall). The proximal tip 144 of the biliary tube segment 140 has a hole 142 for inflow of bile fluid. The internal bolster 146 on the biliary tube segment 140 anchors it inside the gallbladder lumen. As shown in FIG. 11C, the incision is sutured closed to seal the terminal portion of the biliary tube segment 140 inside the gallbladder. As shown in FIG. 11D, a slidable washer 148 fitted around the tube segment is pushed down onto the incision and glued onto the suture site with an adhesive to further improve the seal.

FIG. 12 shows the flush tube segment 150 being attached to the biliary tube segment 140 and the ileal tube segment 130. With the biliary tube segment 140 implanted in the gallbladder and the ileal tube segment 130 implanted inside the ileum, the two tube segments are ready to be joined together. This is performed using a flush tube segment 150 that has a T-connector 152 at its distal end. The distal end of the biliary tube segment 140 is slid into one end of the T-connector 152 and the proximal end of the ileal tube segment 130 is slid into the other end of the T-connector 152. The biliary tube segment 140 and the ileal tube segment 130 are now joined together with each other, as well as with the flush tube segment 150.

The proximal end of the flush tube segment 150 is grasped with a laparoscopic grasper and pulled out of the abdominal cavity through one of the laparoscopy trocar puncture incisions. An external bolster 154 is attached to the proximal end of the flush tube segment 150 to help retain it at the skin surface. A syringe connector 156 is also attached to allow fitting with a syringe (to flush the catheter).

FIG. 13 shows another example of a catheter in which its tube system is provided as three separate components: a biliary tube segment 160, an ileal tube segment 162, and a flush tube segment 164 that are assembled together when the catheter is implanted. The flush tube segment 164 has a terminal portion towards its proximal end that is positioned outside the patient's abdomen (e.g. at the skin surface). There is a flush port 166 at the proximal end of the flush tube segment 164. The flush port 166 can be penetrated with a conventional syringe needle to infuse flush fluid. The terminal portion is fitted with a support brace 168 that serves to retain the flush port 166 at the skin surface. The distal end of the flush tube segment 164 has external threading 176 to mate with the ileal tube segment 162.

The ileal tube segment 162 has a terminal portion towards its distal end for inserting into the patient's ileum. The ileal tube segment 162 has a balloon 170 that can be inflated to help retain the terminal portion inside the ileum. At the distal end of the ileal tube segment 162, there is a drainage hole 172 for draining bile fluid into the ileum. At the proximal end of the ileal tube segment 162, there is a connector segment 174 in which its hollow bore has internal threads 175. During implantation, the flush tube segment 164 is screwed to the ileal tube segment 162 via the threading.

The terminal portion of the biliary tube segment 160 towards its proximal end is for inserting into a patient's gallbladder. On this terminal portion are inlet perforations 177 for draining bile fluid. The biliary tube segment 160 has a circumferential cuff 178 that helps retain the proximal terminal portion inside the gallbladder. The biliary tube segment 160 contains a one-way check valve 161 that facilitates the forward flow of fluid distally or resist the backflow of fluid proximally. The biliary tube segment is connected to the stem 163 on the ileal tube segment 162.

In operation, bile fluid flows into the biliary tube segment 160, through the valve 161, and into the ileal tube segment 162. With the flush port 166 being shut, the bile fluid flows down the ileal tube segment 162 and out into the ileum. To flush the catheter, a needle-tipped syringe is pierced into the flush port 166. The flush fluid in the syringe is infused into the flush port 166, which flows down into the ileal tube segment 162 and out into the ileum.

Figure 14:
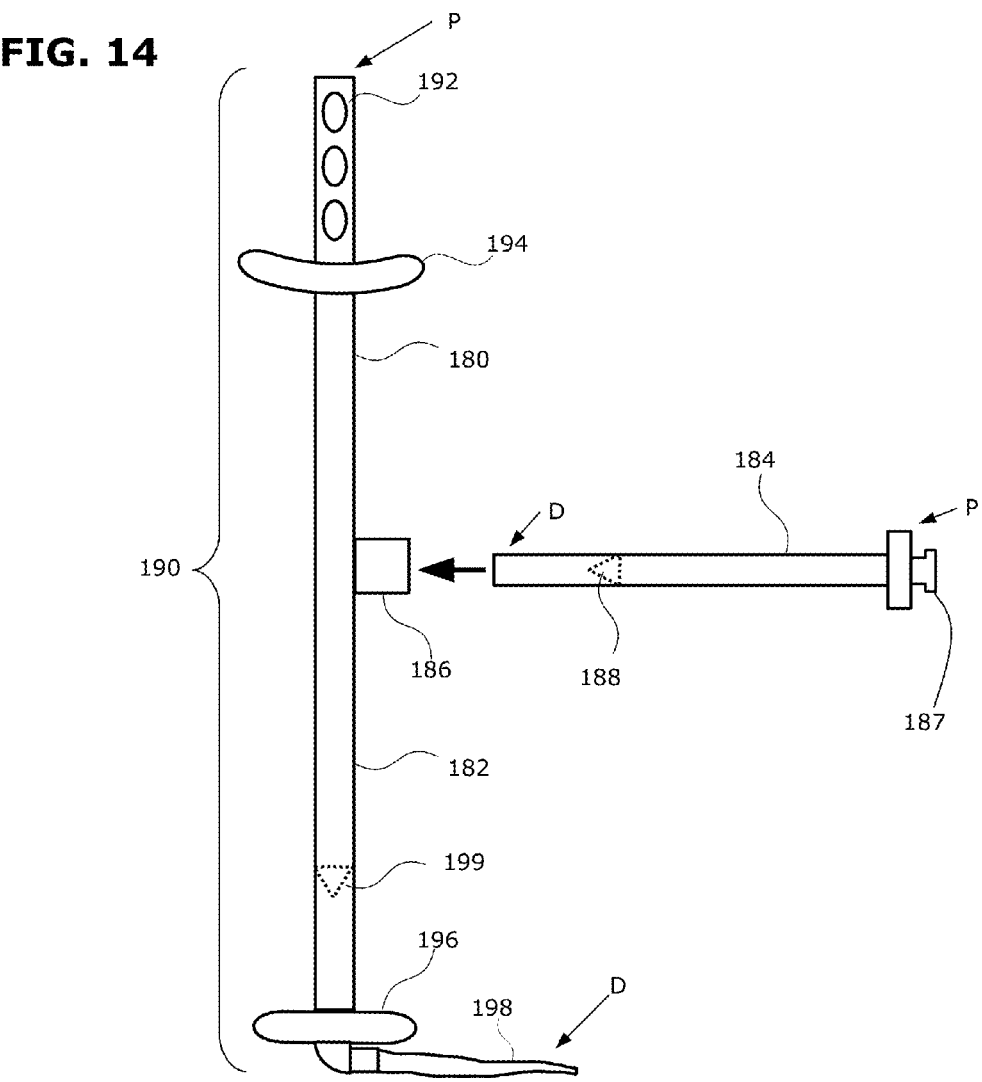
FIG. 14 shows an example of a biliary diversion catheter in which its tube system is provided as two separate components.

In some embodiments, the catheter's tube system is provided as at least two separate tube components that are assembled together when the catheter is implanted. In some embodiments, the tube system is provided as a drainage tube (combining the biliary tube segment and the ileal tube segment) and separately, a flush tube segment. FIG. 14 shows an example of a catheter in which its tube system is provided as two separate components. Here, the biliary tube segment 180 and ileal tube segment 182 are provided as a single drainage tube 190. The flush tube segment 184 is a separate component that is connected to the drainage tube 190 when the catheter is implanted. The drainage tube 190 has a connector seat 186 to receive the distal end of the flush tube segment 184. At the proximal end of the flush tube segment 184 is a Luer fitting 187 (female) for receiving a Luer connector-tipped syringe. The flush tube segment 184 has a one-way valve 188 to facilitate the forward flow of the flush fluid distally. As an example, this catheter could be implanted by first implanting the drainage tube 190 with its proximal terminal portion inside the target site in the biliary tree and the distal terminal portion inside the ileum. Within the abdominal cavity, the flush tube segment 184 is connected to the drainage tube 190. Alternatively, this implantation procedure could be performed according to any other suitable sequence of steps. Other components of the catheter include inlet perforations 192, bumper 194, and duckbill valve 198.

Figure 15:
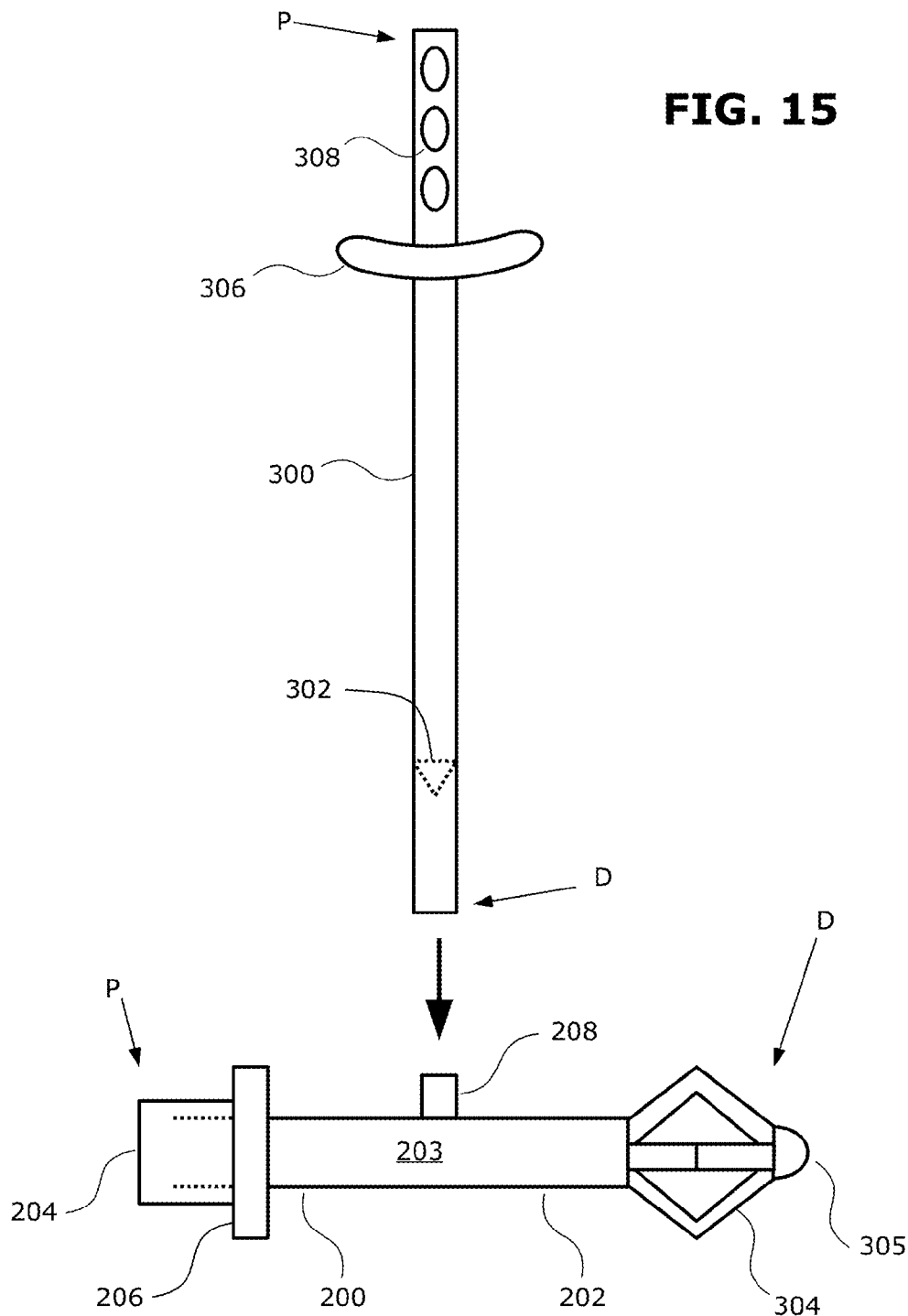
FIG. 15 shows another example of a biliary diversion catheter in which its tube system is provided as two separate components.

In some embodiments, the tube system is provided as a transabdominal tube (combining the flush tube segment and the ileal tube segment) and a separate biliary tube segment. FIG. 15 shows an example of a catheter in which its tube system is provided as two separate components. Here, the flush tube segment 200 and ileal tube segment 202 are provided as a single transabdominal tube 203. At the proximal end of the transabdominal tube 203 (at its flush tube segment 200) is a screw-on cap 204 that fits over the proximal end opening on the transabdominal tube 203. The cap 204 can be screwed off to access the opening to flush the catheter. The proximal terminal portion of the transabdominal tube 203 (at its flush tube segment 200) is retained at the skin surface with the help of the support collar 206. The distal terminal portion of the transabdominal tube 203 (at its ileal tube segment 202) is for inserting into the patient's ileum. At its distal end, the transabdominal tube 203 has an outlet port (not shown) for outflow of bile fluid. Also, the distal end is fitted with an expandable cage 304 and locking hub 305 that helps to retain the distal terminal portion inside the intestine.

The biliary tube segment 300 is a separate component that is connected to the transabdominal tube 203 via a stem 208 when the catheter is implanted. The biliary tube segment 300 has inlet perforations 308 to receive bile fluid and a one-way valve 302 to resist backflow of intestinal contents and to force the flow of flush fluid towards the distal end of the transabdominal tube 203. As an example, this catheter could be implanted by first inserting the biliary tube segment 300 along with its bumper 306 into the gallbladder. The transabdominal tube 203 is then inserted into one of the laparoscopic trocar puncture incisions. The distal terminal portion of the transabdominal tube 203 is inserted into the ileum and anchored in place by deploying (by expanding) the expandable cage 304. The biliary tube segment 300 is connected to the transabdominal tube 203 via its stem 208. Alternatively, this procedure could be performed according to any other suitable sequence of steps.

Figure 16:
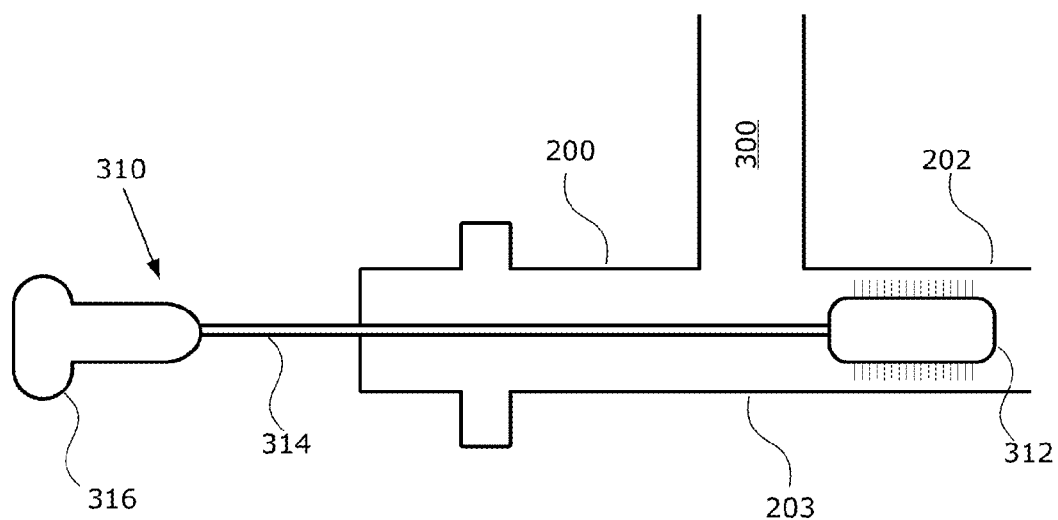
FIG. 16 shows an endoluminal cleaning tool.

FIG. 16 shows an endoluminal cleaning tool 310 that could be used to clean the catheter shown in FIG. 15. This shows a cross-section side view of the catheter with the cap on the transabdominal tube 203 removed so that the cleaning tool 310 can be inserted. The flush tube segment 200, ileal tube segment 202, biliary tube segment 300, and transabdominal tube 203 are labeled. The cleaning tool 310 has a brush head 312 mounted on a steerable cable 314. A handle 316 is provided so that the user can clean the transabdominal tube 203 with a back-and-forth or twisting motion of the brush head 312. The cleaning tool 310 could also be steered upward to snake the brush head 312 into the biliary tube segment 300 for cleaning as well.

Figure 17A:
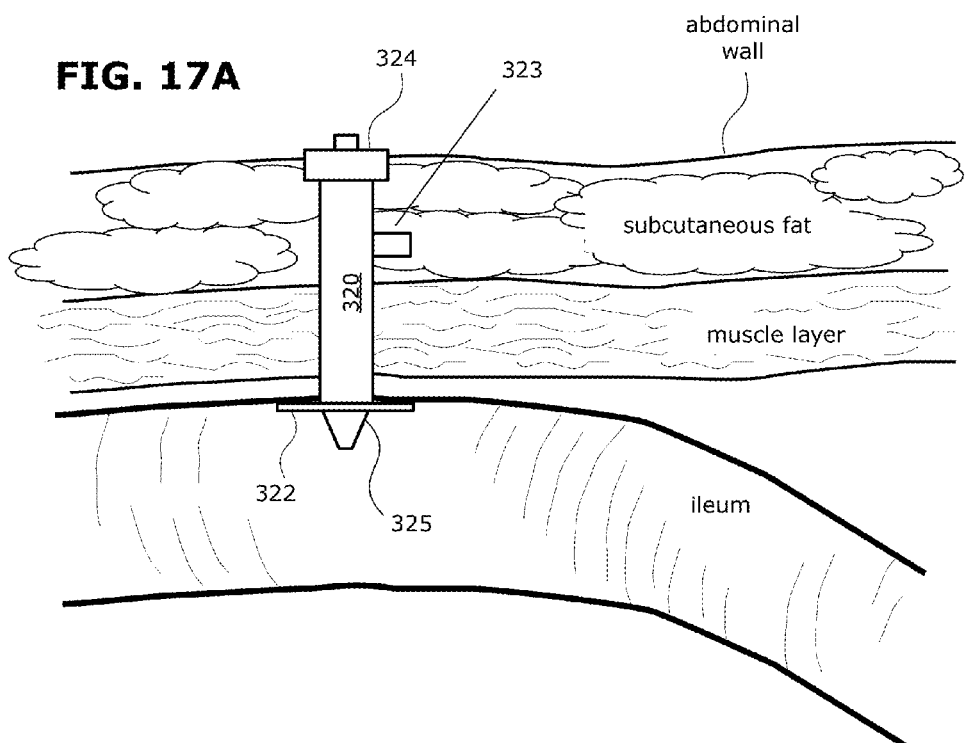
FIGS. 17A and 17B show another example of a biliary diversion catheter and how it could be implanted.
Figure 17B:
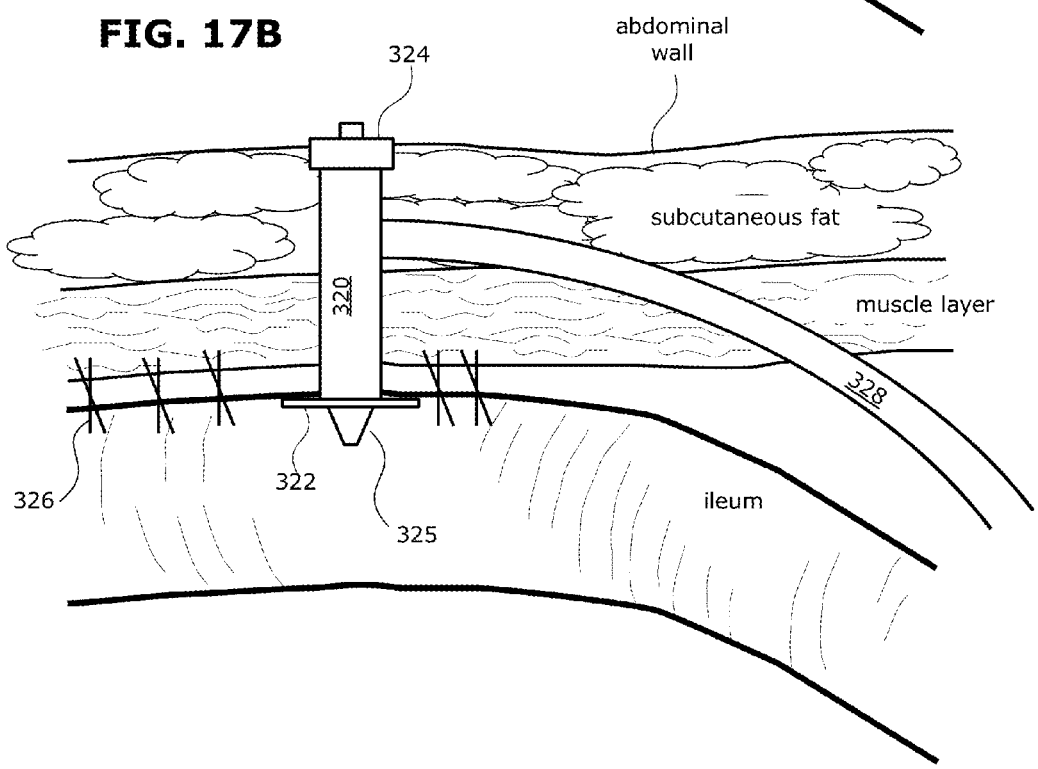

FIGS. 17A and 17B show another example of a catheter and how it could be implanted. FIG. 17A shows the transabdominal tube 320 traversing through the abdominal wall with its distal terminal portion inside the ileum. At its distal end, there is a duckbill valve 325 for draining out bile fluid. The transabdominal tube 320 is anchored by a thin mesh 322 that is sutured to the ileal wall. The proximal terminal portion of the transabdominal tube 320 is outside the abdominal cavity with its syringe connector 324 at the skin surface. As shown in FIG. 17B, the portion of the ileum near the insertion site is fixed to the abdominal wall by anchoring stitches 326. Attaching the ileum to the abdominal wall in this manner helps to prevent torsion of the small intestine. A tunnel is made in the abdominal wall leading from the transabdominal tube 320 to the peritoneal space inside the abdominal cavity. The biliary tube segment 328 is passed through the tunnel and its distal end is connected to the transabdominal tube 320 via its stem 323. The proximal terminal portion of the biliary tube segment 328 (not shown) is inserted into a part of the biliary tree.

Examples of Other Components.

Figure 18A:
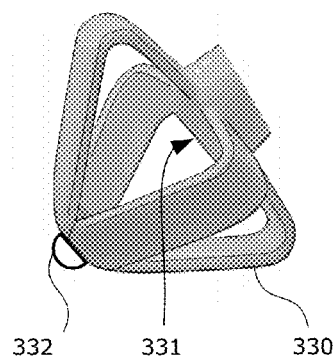
FIGS. 18A-18E show other examples of types of configurations for the terminal portion of the biliary tube segment or the ileal tube segment.
Figure 18B:
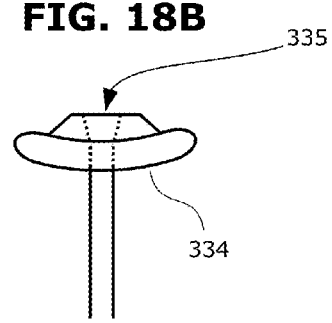

FIGS. 18A-18E shows other examples of types of configurations for the terminal portion of the biliary tube segment or the intestinal tube segment. FIG. 18A shows a star-shaped flexible retention bolster at the terminal portion of a tube. The retention bolster has flexible arms 330 that join at a hub 332. Flexible arms 330 can be collapsed into a cylindrical shape (radially retracted state) to facilitate insertion or radially expanded into a rivet shape to help anchor the terminal portion of the tube in the relevant body organ. There is an opening 331 at the terminal end of the tube to allow inflow or outflow of bile fluid. FIG. 18B shows a button 334 with a funnel port 335 at the terminal end of a tube. The button 334 can help anchor the terminal portion of the tube in the relevant body organ. The funnel port 335 allows inflow or outflow of bile fluid.

Figure 18C:
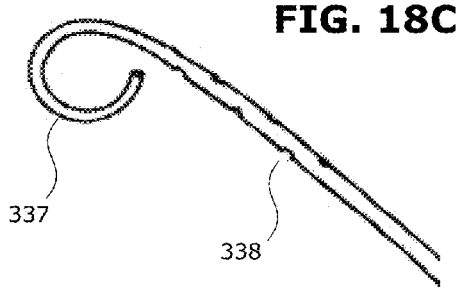
Figure 18D:
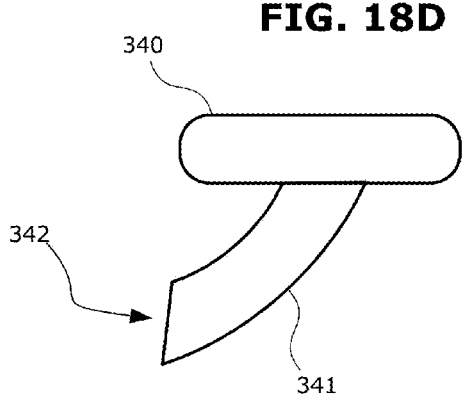
Figure 18E:
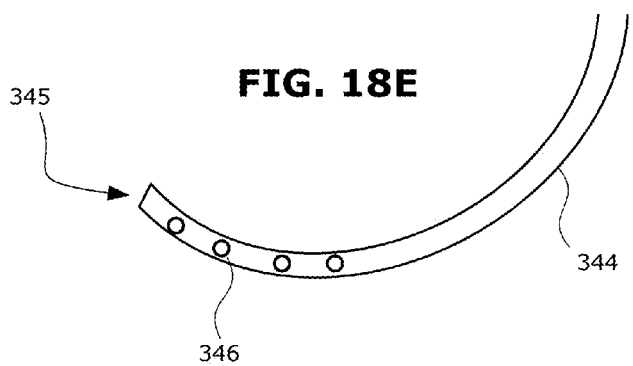

FIG. 18C shows the terminal portion of a tube in a pigtail coil configuration. This pigtail coil 337 can help anchor the terminal portion of the tube in the relevant body organ. The tube has perforations 338 to allow inflow or outflow of bile fluid. FIG. 18D shows a shoulder 340 at the terminal portion of a tube. The terminal portion of the tube has a curved shape 341 with an opening 342 at its tip to allow inflow or outflow of bile fluid. FIG. 18E shows the terminal portion of a flexible tube 344 having a closed tip 345. The tube has perforations 346 to allow inflow or outflow of bile fluid.

Figure 19A:
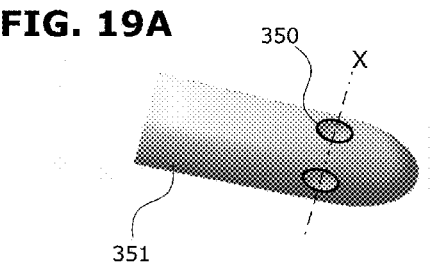
FIGS. 19A and 19B, and FIGS. 20A-20C show an example of a three-way directional control valve.
Figure 19B:
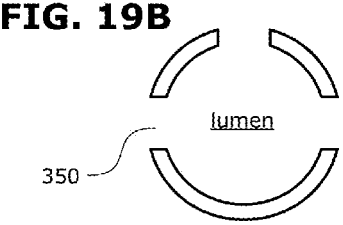
Figure 20A:
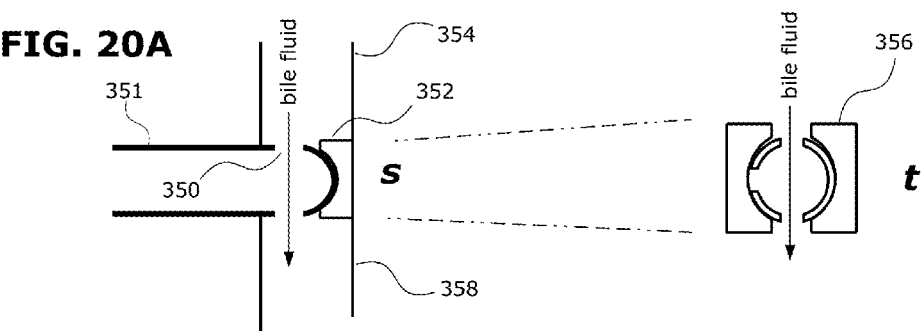
Figure 20B:
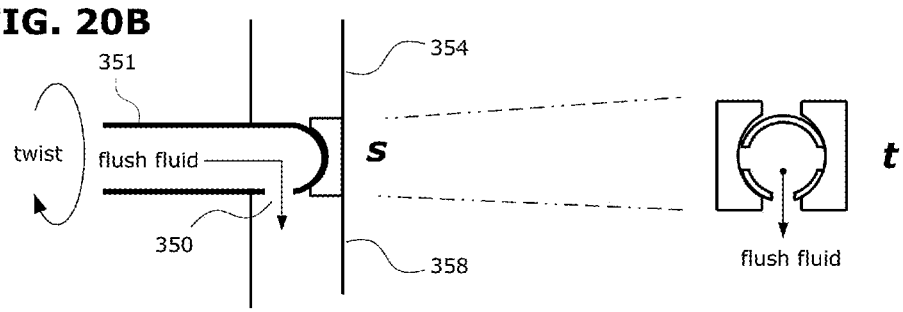
Figure 20C:
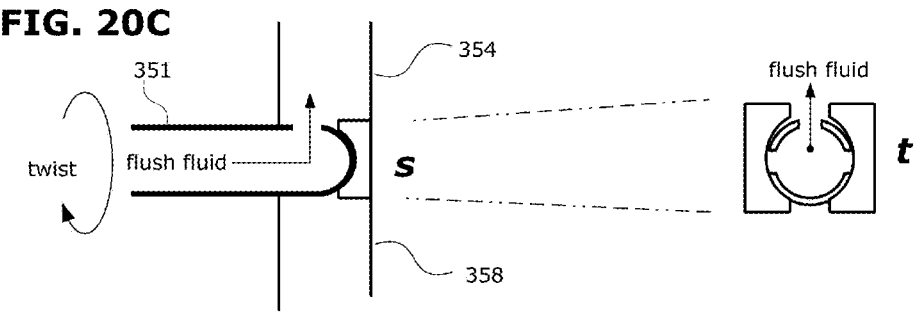

FIGS. 19A and 19B, and FIGS. 20A-20C show an example of a three-way directional control valve. FIG. 19A shows the distal end of a flush tube segment 351 having three apertures 350 that allow the distal end of the flush tube segment 351 to operate as a directional control valve. FIG. 19B is a transverse cross-section view of the flush tube segment 351 at line X and shows the position of the three apertures. FIGS. 20A-20C shows the directional control valve in operation. In FIG. 20A, the left panel side view ("s") shows that the flush tube segment 351 intersects with the biliary tube segment 354 and the ileal tube segment 358. The distal tip of the flush tube segment 351 is braced against an end seat 352 that forms a seal with the distal tip. In this scenario, the apertures 350 on the flush tube segment 351 are oriented so that bile fluid can pass through from the biliary tube segment 354 into the ileal tube segment 358. The right panel shows a transverse cross-section view ("t") taken along the plane crossing the apertures 350. The sides of the flush tube segment 351 rest against lateral seats 356 that seal the sides of the flush tube segment 351. As seen here, the top and bottom apertures 350 are exposed so that bile fluid can pass through, but the side-facing aperture 350 is sealed against the lateral seat 356.

The flush tube segment 351 can be twisted on its axis to change the flow direction. In FIG. 20B, the flush tube segment 351 has been twisted one-quarter turn so that the flush fluid infused through the flush tube segment 351 flows down into the ileal tube segment 358, but not the biliary tube segment 354. As seen in the right panel transverse cross-section view ("t"), the apertures 350 facing left and right are sealed against the lateral seats 356. However, the aperture 350 at the bottom is exposed, which allows the flush fluid to flow into the ileal tube segment 358.

In FIG. 20C, the flush tube segment 351 has been further twisted one-half turn so that the flush fluid infused through the flush tube segment 351 flows up into the biliary tube segment 354, but not the ileal tube segment 358. As seen in the right panel transverse cross-section view ("t"), the apertures 350 facing left and right are sealed against the lateral seats 356. However, the aperture 350 at the top is exposed, which allows the flush fluid to flow into the biliary tube segment 354. Having a directional control valve such as this can be useful for allowing the user to flush the biliary tube segment 354 and the ileal tube segment 358 separately.

Figure 21A:
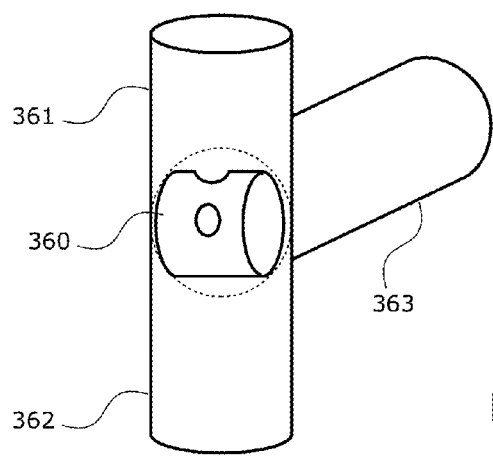
FIGS. 21A, 21B, and 22A-22C show another example of a three-way directional control valve.
Figure 21B:
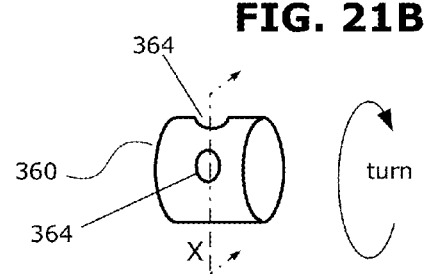
Figure 22A:
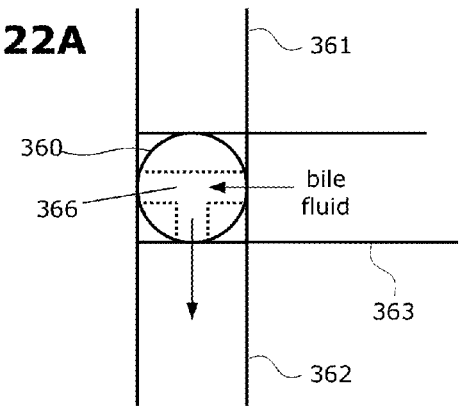
Figure 22B:
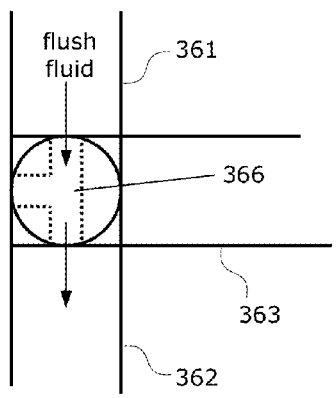
Figure 22C:
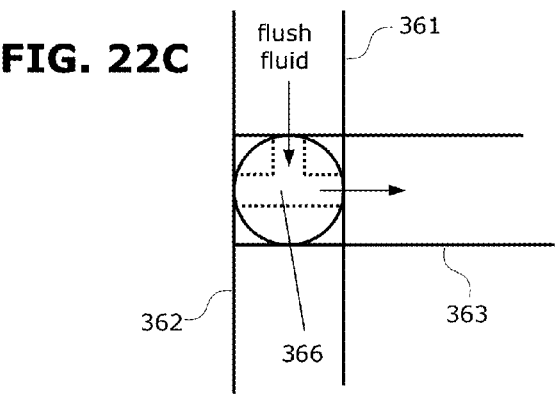

FIGS. 21A, 21B, and 22A-22C show another example of a three-way directional control valve 360. FIG. 21A shows the directional control valve 360 positioned at the intersection of the flush tube segment 361, the biliary tube segment 363, and the ileal tube segment 362. The valve 360 has a T-shaped channel 366 and three channel openings 364. FIG. 21B shows the valve 360 in isolation, with two of the three channel openings 364 being visible. Turning the valve 360 changes the direction in which the channel openings 364 face. FIGS. 22A-22C show the directional control valve 360 in operation with transverse cross-section views taken at the line X in FIG. 21B. FIG. 22A shows the control valve 360 in a pose for bile fluid drainage. Bile fluid flows into the biliary tube segment 363, enters the channel 366 of the valve 360, and is diverted towards the ileal tube segment 362.

FIG. 22B shows the control valve 360 turned one-quarter turn. In this pose, the ileal tube segment 362 can be flushed. The external opening on the flush tube segment 361 is accessed and flush fluid is infused into the flush tube segment 361. The flush fluid flows through the flush tube segment 361 and down into the ileal tube segment 362 only. The biliary tube segment 363 is blocked because there is no channel opening 364 facing the biliary tube segment 363. FIG. 22C shows the control valve 360 further turned another one-quarter turn. In this pose, the biliary tube segment 363 can be flushed. The opening on the flush tube segment 361 is accessed and flush fluid is infused into the flush tube segment 361. The flush fluid flows through the flush tube segment 361 and into the biliary tube segment 363 only. The ileal tube segment 362 is blocked because there is no channel opening 364 facing the ileal tube segment 362. Having a directional control valve 360 such as this can be useful for allowing the user to flush the biliary tube segment 363 and the ileal tube segment 362 separately.

Figure 23A:
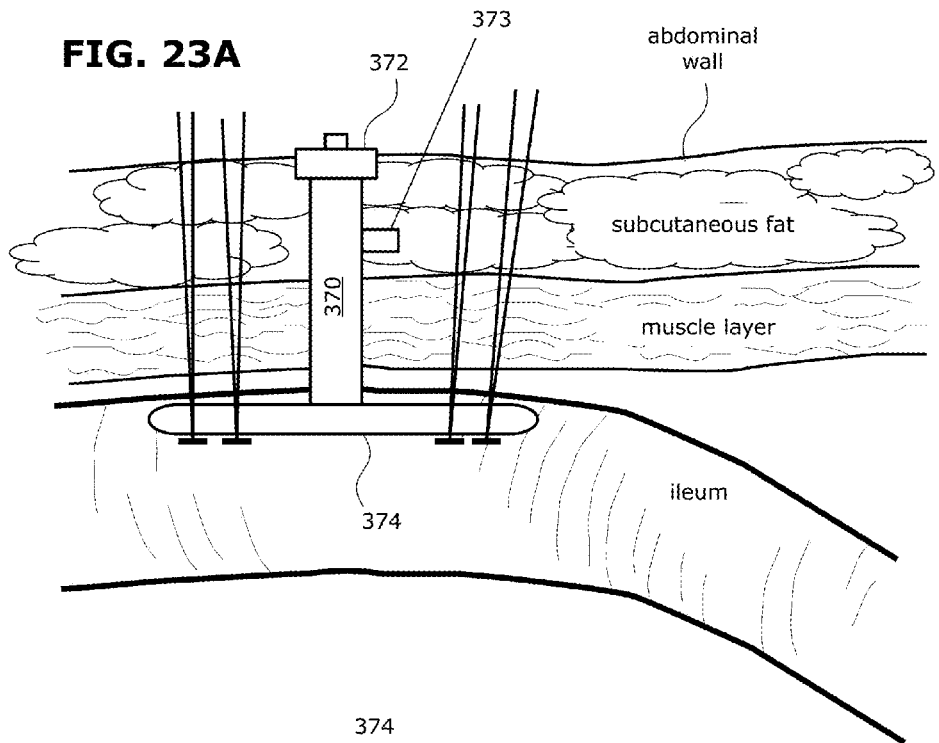
FIGS. 23A and 23B show another example of a retention anchor and how it could used to implant a catheter.
Figure 23B:
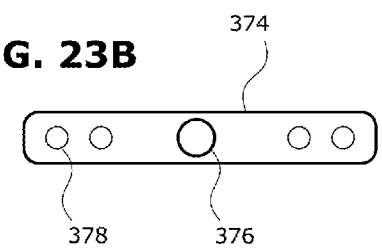
Figure 23C:
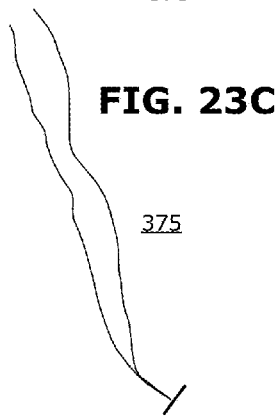
FIG. 23C shows a T-anchor suture.

FIGS. 23A and 23B show another example of a retention anchor and how it could used to implant a catheter. FIG. 23A shows a transabdominal tube 370 passing through the abdominal wall with its distal terminal portion inside the ileum. The proximal terminal portion of the transabdominal tube 370 is outside the abdominal cavity with its syringe connector 372 at the skin surface. As shown in FIG. 23B, the retention saddle 374 has multiple eyelets 378 for receiving a T-anchor suture 375 (see FIG. 23C). The drainage port 376 is the outlet for the bile fluid. To fix the ileum to the abdominal wall, the T-anchors 375 are passed through the abdominal wall (e.g. using a needle), passed into the ileum, and secured to the retention saddle 374 through the eyelets 378. Externally, the transabdominal T-anchor sutures 375 are pulled to draw the ileum against the inner abdominal wall and tied. The biliary tube segment is connected to the transabdominal tube 370 via its stem 373 in the same manner as described for FIG. 17 above.

Figure 24A:
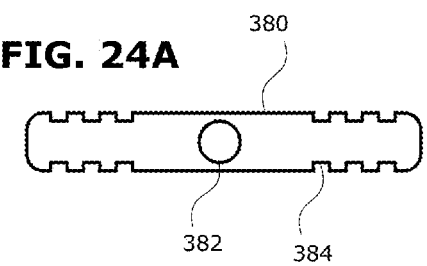
FIGS. 24A and 24B show another example of a retention anchor.
Figure 24B:
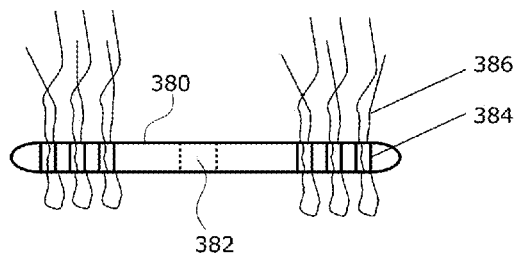

FIGS. 24A and 24B show another example of a retention anchor. As shown in FIG. 24A, this retention anchor is a saddle 380 at the distal end of the ileal tube segment. The drainage port 382 of the ileal tube segment passes through the saddle 380. The saddle 380 also has multiple suture notches 384 to help retain sutures 386. As shown in FIG. 24B, sutures 386 are embedded into the notches 384 and wound around the saddle 380. These sutures 386 are then passed through the abdominal wall and pulled to draw the ileum against the inner abdominal wall. The sutures 386 are then tied to fix the ileum to the abdominal wall.

Figure 25:
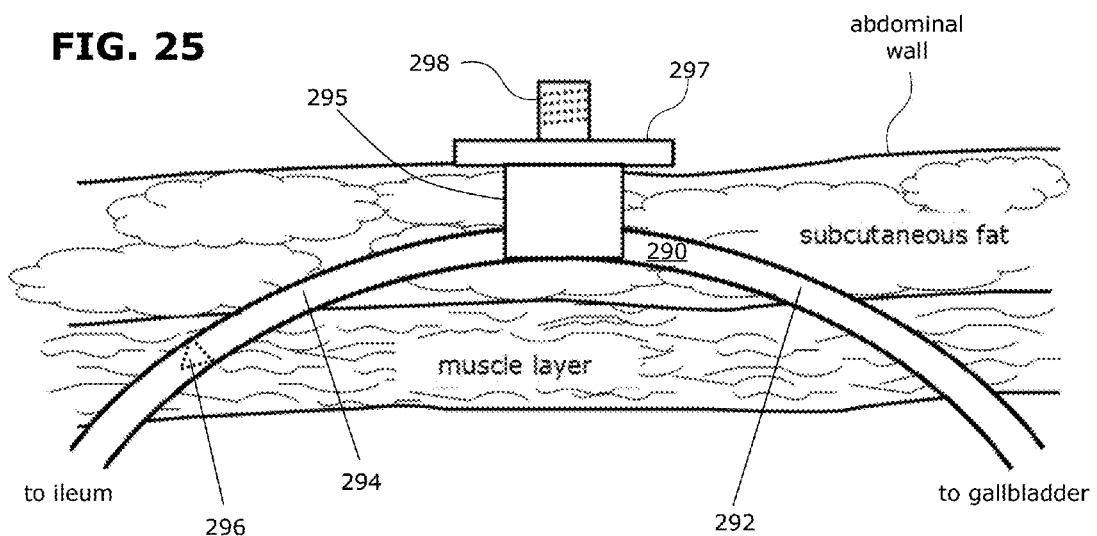
FIG. 25 shows another example of a biliary diversion catheter as fully implanted in the patient's abdomen.

FIG. 25 shows another example of a catheter as fully implanted in the patient's abdomen. This catheter comprises a drainage tube 290 (which comprises a biliary tube segment 292 and an intestinal tube segment 294. The drainage tube 290 travels through a tunnel created within the abdominal wall.

On the left side of the drawing, the intestinal tube segment 294 of the drainage tube 290 exits out of the tunnel into the peritoneum. The distal terminal portion of the intestinal tube segment 294 (not shown) is inserted into the ileum. On the right side of the drawing, the biliary tube segment 292 exits out of the tunnel into the peritoneum. The proximal terminal portion of the biliary tube segment 292 (not shown) is inserted into the gallbladder (not shown). Bile fluid in the gallbladder flows into the biliary tube segment 292 and drains out into the ileum via the intestinal tube segment 294.

The flush tube segment 295 connects to the drainage tube 290 at its intermediate portion between the biliary tube segment 292 and intestinal tube segment 294. The proximal terminal portion of the flush tube segment 295 rests on the skin surface of the abdominal wall. On this proximal terminal portion, there is a Luer connector 298 with internal threads to connect with a Luer adaptor on a syringe or conventional intravenous (IV) line for infusing flush fluid. A plastic disc 297 fitted around Luer connector 298 helps retain it at the skin surface (instead of being withdrawn into the abdominal wall).

Figure 26A:
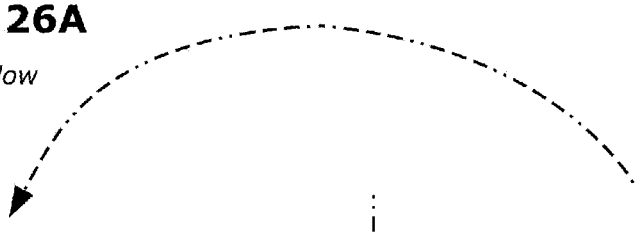
FIGS. 26A-26C show the flow of fluid under directional control by the 3-way valve.
Figure 26B:
Figure 26C:
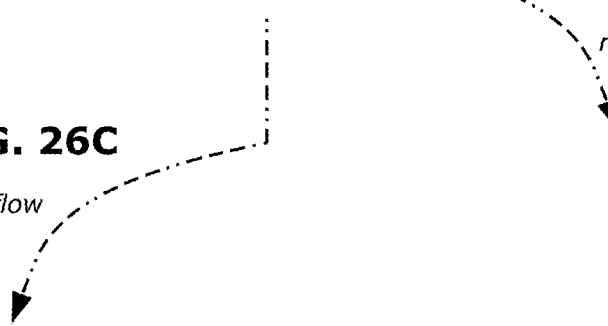

The flush tube segment 295 houses a 3-way valve that selectively permits flow within the tube system. FIGS. 26A-26C show the flow of fluid under directional control by the 3-way valve. In FIG. 26A, the 3-way valve is in a pose that allows flow of bile fluid through the biliary tube segment 292, across the valve, and then through the intestinal tube segment 294. However, flow of bile fluid up into the flush tube segment 295 is blocked. In FIG. 26B, the 3-way valve is in a pose that directs flow of flush fluid from the flush tube segment 295 in reverse direction through the biliary tube segment 292 to help clear any obstructions in this section of the catheter. However, flow of flush fluid into the intestinal tube segment is blocked. In FIG. 26C, the 3-way valve is in a pose that directs flow of flush fluid from the flush tube segment 295 in forward direction through the intestinal tube segment 294 to help clear any obstructions in this section of the catheter. However, flow of flush fluid into the biliary tube segment 292 is blocked.

Figure 27A:
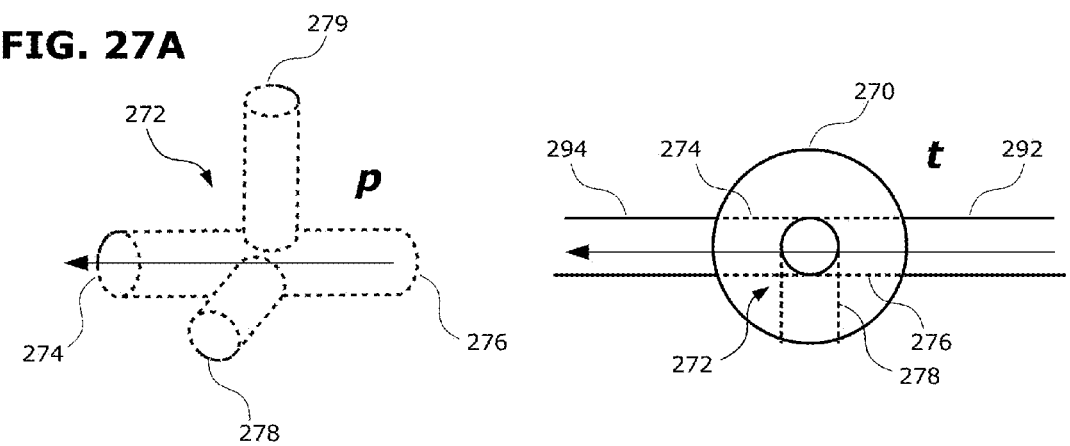
FIGS. 27A-27C show the operation of the 3-way valve within the flush tube segment.
Figure 27B:
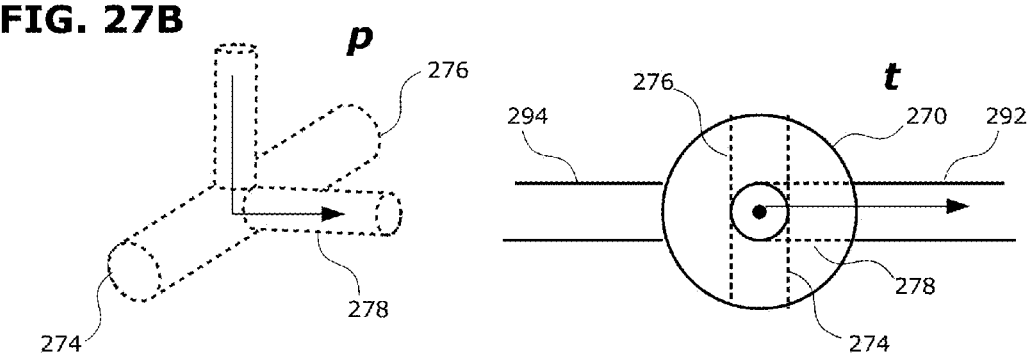
Figure 27C:
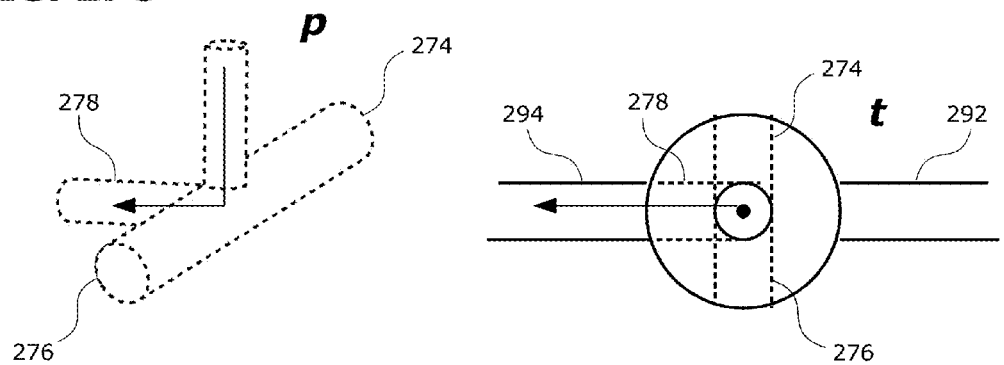

FIGS. 27A-27C show the operation of the 3-way valve 270 within the flush tube segment 295. The left column (p) shows a perspective view of the internal channel structure 272 of the 3-way valve in isolation. The right column (t) show top, cross-section views of the valve 270 that indicate the orientation of the internal channels and the direction of fluid flow. Inside the valve 270, there is a channel structure 272 through which fluid flows. Channel portion 279 receives the flush fluid. Channel portions 274, 276, and 278 can be turned towards different directions to direct the flow of fluid. The valve 270 is operated by turning it so that channel portions 274, 276, and 278 can have different orientations within the flush tube segment 295, i.e. are made to face the biliary tube segment 292, or intestinal tube segment 294, or be sealed.

Referring to FIG. 27A, in the normal bile fluid drainage mode of operation, the valve 270 is turned so that channel portions 274 and 276 are aligned with the lumen of the intestinal tube segment 294 and the biliary tube segment 292. This permits the flow of biliary fluid from the biliary segment 292 into the intestinal tube segment 294. Referring to FIG. 27B, this configuration is for flushing the biliary segment 292. The 3-way valve 270 is turned so that channel portion 278 is aligned with the biliary tube segment 292. This permits flush fluid to flow into the biliary tube segment 292, thereby flushing the biliary tube segment 292. However, the position of the 3-way valve 270 blocks the flow of flush fluid into the intestinal tube segment 294. Referring to FIG. 27C, this configuration is for flushing the intestinal tube segment 294. The 3-way valve 270 is turned so that channel portion 278 is aligned with the intestinal tube segment 294. This permits flush fluid to flow into the intestinal tube segment 294, thereby flushing the intestinal tube segment 294. However, the position of the 3-way valve 270 blocks the flow of flush fluid into the biliary tube segment 292.

The foregoing description and examples have been set forth merely to illustrate my invention and are not intended to be limiting. Each of the disclosed aspects and embodiments of my invention may be considered individually or in combination with other aspects, embodiments, and variations of my invention. In addition, unless otherwise specified, the steps of the methods of my invention are not confined to any particular order of performance. Modifications of the disclosed embodiments incorporating the spirit and substance of my invention may occur to persons skilled in the art, and such modifications are within the scope of my invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

The invention claimed is:

1. A biliary diversion catheter that comprises a tube system, the tube system comprising:
    a biliary tube segment;
    an intestinal tube segment that is in fluid communication with the biliary tube segment;
    a flush tube segment that is in fluid communication with the intestinal tube segment;
    a directional control valve that is operable to control a flow of fluid between the flush tube segment and the intestinal tube segment or biliary tube segment;
    wherein the biliary tube segment has a proximal end and a proximal terminal portion encompassing the proximal end of the biliary tube segment, and wherein the proximal terminal portion comprises an opening configured to allow inflow of bile fluid into the biliary tube segment;
    wherein the intestinal tube segment has a distal end and a distal terminal portion that encompasses the distal end of the intestinal tube segment, and wherein the distal terminal portion comprises an opening configured to allow outflow of bile fluid;
    wherein the flush tube segment has a proximal end and a proximal terminal portion that encompasses the proximal end of the flush tube segment, and wherein the proximal terminal portion comprises an opening configured to receive flush fluid;
    wherein the directional control valve has:
    a first pose that gives fluid communication between the biliary tube segment and the intestinal tube segment, but not the flush tube segment, and configured to allow flow of bile fluid from the biliary tube segment into the intestinal tube segment;
    a second pose that gives fluid communication between the flush tube segment and the intestinal tube segment, but not the biliary tube segment, and configured to allow flushing in a forward direction within the intestinal tube segment; and
    a third pose that gives fluid communication between the flush tube segment and the biliary tube segment, but not the intestinal tube segment, and configured to allow flushing in a reverse direction within the biliary tube segment.

2. The biliary diversion catheter of claim 1, wherein when flush fluid is infused into the flush tube segment, the flush fluid flows at least into the intestinal tube segment.

3. The biliary diversion catheter of claim 1, wherein the distal terminal portion of the intestinal tube segment comprises a retention anchor.

4. The biliary diversion catheter of claim 1, wherein the proximal terminal portion of the flush tube segment comprises a retention anchor.

5. The biliary diversion catheter of claim 1, wherein the proximal terminal portion of the biliary tube segment comprises a retention anchor.

6. The biliary diversion catheter of claim 1, wherein the intestinal tube segment comprises a one-way valve that permits fluid flow towards the distal end of the intestinal tube segment, but impedes fluid flow in a proximal direction across the valve.

7. The biliary diversion catheter of claim 1, wherein the biliary tube segment and the intestinal tube segment together form a drainage tube.

8. The biliary diversion catheter of claim 7, wherein the flush tube segment is provided separately and the biliary diversion catheter is assembled by connecting the flush tube segment to the drainage tube.

9. The biliary diversion catheter of claim 1, wherein the flush tube segment and the intestinal tube segment together form a transabdominal tube.

10. The biliary diversion catheter of claim 9, wherein the biliary tube segment is provided separately and the biliary diversion catheter is assembled by connecting the biliary tube segment to the transabdominal tube.

11. The biliary diversion catheter of claim 1, wherein the biliary tube segment and the intestinal tube segment together form an anastomotic component.

12. The biliary diversion catheter of claim 11, wherein the biliary tube segment and the intestinal tube segment are provided separately and the anastomotic component is assembled by connecting the biliary tube segment to the intestinal tube segment.

13. The biliary diversion catheter of claim 11, wherein the tube system is configured such that the flush tube segment can selectively flush either the biliary tube segment or the intestinal tube segment of the anastomotic component.

14. The biliary diversion catheter of claim 1, further comprising a syringe port at the proximal terminal portion of the flush tube segment, wherein the syringe port comprises the opening to receive flush fluid.

15. The biliary diversion catheter of claim 14, further comprising a cap for covering the syringe port.

16. The biliary diversion catheter of claim 1, the biliary tube segment further comprising a one-way valve that facilitates the forward flow of fluid distally or resists the backflow of fluid proximally.

17. The biliary diversion catheter of claim 9, the biliary tube segment further comprising a one-way valve that facilitates the forward flow of fluid distally or resists the backflow of fluid proximally.

18. The biliary diversion catheter of claim 1, wherein the biliary tube segment, the intestinal tube segment, and the flush tube segment are provided as separate components that are assembled together.

19. The biliary diversion catheter of claim 7, wherein the flush tube segment is provided separately from the drainage tube.

20. The biliary diversion catheter of claim 9, wherein the biliary tube segment, the intestinal tube segment, and the flush tube segment are provided as separate components that are assembled together.

* * * * *